(12) United States Patent
Sherman et al.

(10) Patent No.: US 8,758,237 B2
(45) Date of Patent: Jun. 24, 2014

(54) METHODS AND PRODUCTS FOR ILLUMINATING TISSUE

(75) Inventors: Audrey A. Sherman, St. Paul, MN (US); Matthew T. Scholz, Woodbury, MN (US); Michael A. Meis, Stillwater, MN (US); Kevin R. Schaffer, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 180 days.

(21) Appl. No.: 13/391,221

(22) PCT Filed: Aug. 19, 2010

(86) PCT No.: PCT/US2010/045956
§ 371 (c)(1),
(2), (4) Date: May 4, 2012

(87) PCT Pub. No.: WO2011/022525
PCT Pub. Date: Feb. 24, 2011

(65) Prior Publication Data
US 2012/0215073 A1    Aug. 23, 2012

Related U.S. Application Data

(60) Provisional application No. 61/236,027, filed on Aug. 21, 2009.

(51) Int. Cl.
*A61B 1/06* (2006.01)
*A61B 19/08* (2006.01)

(52) U.S. Cl.
USPC ........................................... 600/249

(58) Field of Classification Search
USPC ......... 600/206, 204, 205, 208, 210, 212, 245, 600/249; 362/615, 616, 618, 622, 627, 629; 606/1; 128/849–852
See application file for complete search history.

(56) References Cited

U.S. PATENT DOCUMENTS

| | | |
|---|---|---|
| 2,736,721 A | 2/1956 | Dexter |
| 3,347,226 A | 10/1967 | Harrower |
| 3,822,238 A | 7/1974 | Blair |
| 3,975,350 A | 8/1976 | Hudgin |
| 4,231,369 A | 11/1980 | Sorensen |
| 4,310,509 A | 1/1982 | Berglund |
| 4,323,557 A | 4/1982 | Rosso |
| 4,369,294 A | 1/1983 | Stoy |
| 4,379,874 A | 4/1983 | Stoy |
| 4,420,589 A | 12/1983 | Stoy |

(Continued)

FOREIGN PATENT DOCUMENTS

| WO | WO 84/01285 | 4/1984 |
|---|---|---|
| WO | WO 95/17303 | 6/1995 |

(Continued)

OTHER PUBLICATIONS

ASTM D412—06a, Standard Test methods for Vulcanized Rubber Thermoplastic Elastomers—Tension, 2006, 14 pages.

(Continued)

*Primary Examiner* — Pedro Philogene
(74) *Attorney, Agent, or Firm* — Thomas M. Spielbauer

(57) ABSTRACT

Methods and products for illuminating the tissue of a patient wherein the products include a conformable polymeric layer.

13 Claims, 3 Drawing Sheets

(56) References Cited

U.S. PATENT DOCUMENTS

| | | | |
|---|---|---|---|
| 4,452,845 A | 6/1984 | Lloyd | |
| 4,454,309 A | 6/1984 | Gould | |
| 4,477,325 A | 10/1984 | Osburn | |
| 4,499,896 A | 2/1985 | Heinecke | |
| RE31,886 E | 5/1985 | Hodgson | |
| RE31,887 E * | 5/1985 | Hodgson | 428/355 EN |
| 4,542,012 A | 9/1985 | Dell | |
| 4,551,490 A | 11/1985 | Doyle | |
| 4,554,324 A | 11/1985 | Husman | |
| 4,584,192 A | 4/1986 | Dell | |
| 4,737,559 A | 4/1988 | Kellen | |
| 4,738,257 A | 4/1988 | Meyer | |
| 4,777,943 A | 10/1988 | Chvapil | |
| 4,820,279 A | 4/1989 | Dedo | |
| 5,087,499 A | 2/1992 | Sullivan | |
| 5,214,119 A | 5/1993 | Leir | |
| 5,270,358 A | 12/1993 | Asmus | |
| 5,369,155 A | 11/1994 | Asmus | |
| 5,506,279 A | 4/1996 | Babu | |
| 5,524,644 A | 6/1996 | Crook | |
| 5,593,395 A | 1/1997 | Martz | |
| 5,633,010 A | 5/1997 | Chen | |
| 5,709,646 A | 1/1998 | Lange | |
| 5,730,994 A | 3/1998 | Askill | |
| 5,750,134 A | 5/1998 | Scholz | |
| 5,803,086 A | 9/1998 | Scholz | |
| 5,825,543 A | 10/1998 | Ouderkirk | |
| 5,828,488 A | 10/1998 | Ouderkirk | |
| 5,829,422 A | 11/1998 | Deeds | |
| 5,867,316 A | 2/1999 | Carlson | |
| 5,882,774 A | 3/1999 | Jonza | |
| 5,979,450 A | 11/1999 | Baker | |
| 5,985,395 A | 11/1999 | Comstock | |
| 6,033,604 A | 3/2000 | Lundin | |
| 6,083,856 A | 7/2000 | Joseph | |
| 6,179,948 B1 | 1/2001 | Merrill | |
| 6,216,699 B1 | 4/2001 | Cox | |
| 6,264,976 B1 | 7/2001 | Heinecke | |
| 6,288,172 B1 | 9/2001 | Goetz | |
| 6,352,761 B1 | 3/2002 | Hebrink | |
| 6,367,941 B2 | 4/2002 | Lea | |
| 6,368,699 B1 | 4/2002 | Gilbert | |
| 6,566,575 B1 | 5/2003 | Stickels | |
| 6,663,978 B1 | 12/2003 | Olson | |
| 6,827,886 B2 | 12/2004 | Neavin | |
| 6,845,212 B2 | 1/2005 | Gardiner | |
| 6,855,386 B1 | 2/2005 | Daniels | |
| 6,927,900 B2 | 8/2005 | Liu | |
| 6,939,296 B2 * | 9/2005 | Ewers et al. | 600/206 |
| 6,939,936 B2 | 9/2005 | Wang | |
| 6,972,813 B1 | 12/2005 | Toyooka | |
| 6,991,695 B2 | 1/2006 | Tait | |
| 7,030,203 B2 | 4/2006 | Mosbey | |
| 7,046,905 B1 | 5/2006 | Gardiner | |
| 7,090,922 B2 | 8/2006 | Zhou | |
| 7,255,920 B2 | 8/2007 | Everaerts | |
| 7,315,418 B2 | 1/2008 | DiZio | |
| 7,361,474 B2 | 4/2008 | Siegler | |
| 7,459,167 B1 | 12/2008 | Sengupta | |
| 7,481,563 B2 | 1/2009 | David | |
| 2003/0034445 A1 | 2/2003 | Boyd | |
| 2006/0084780 A1 | 4/2006 | Hebrink | |
| 2006/0216524 A1 | 9/2006 | Klun | |
| 2006/0226561 A1 | 10/2006 | Merrill | |
| 2007/0047080 A1 | 3/2007 | Stover | |
| 2007/0147947 A1 | 6/2007 | Stenton | |
| 2007/0153548 A1 * | 7/2007 | Hamada et al. | 362/615 |
| 2007/0223252 A1 * | 9/2007 | Lee et al. | 362/615 |
| 2008/0046004 A1 | 2/2008 | Stenton | |
| 2008/0232135 A1 | 9/2008 | Kinder | |
| 2009/0067151 A1 | 3/2009 | Sahlin | |
| 2009/0105437 A1 | 4/2009 | Determan | |
| 2009/0116801 A1 | 5/2009 | Fine | |
| 2010/0142222 A1 * | 6/2010 | Vahabzadeh | 362/615 |
| 2010/0222496 A1 | 9/2010 | Determan | |
| 2011/0134623 A1 | 6/2011 | Sherman | |
| 2011/0176325 A1 | 7/2011 | Sherman | |
| 2011/0182076 A1 | 7/2011 | Sherman | |
| 2012/0100039 A1 | 4/2012 | Appeaning | |

FOREIGN PATENT DOCUMENTS

| | | |
|---|---|---|
| WO | WO 95/17691 | 6/1995 |
| WO | WO 95/17692 | 6/1995 |
| WO | WO 95/17699 | 6/1995 |
| WO | WO 96/19347 | 6/1996 |
| WO | WO 97/01440 | 1/1997 |
| WO | WO 98/51352 | 11/1998 |
| WO | WO 99/36248 | 7/1999 |
| WO | WO 99/36262 | 7/1999 |
| WO | WO 99/42536 | 8/1999 |
| WO | WO 00/56828 | 9/2000 |
| WO | WO 00/78885 | 12/2000 |
| WO | WO 02/070237 | 9/2002 |
| WO | WO 2008/022007 | 2/2008 |
| WO | WO 2008/047059 | 4/2008 |
| WO | WO 2009/088757 | 7/2009 |
| WO | WO 2009/091682 | 7/2009 |
| WO | WO 2011/022023 | 2/2011 |
| WO | WO 2011/022525 | 2/2011 |
| WO | WO 2011/022527 | 2/2011 |

OTHER PUBLICATIONS

ASTM D5279—08, Standard Test Method for Plastics: Dynamic Mechanical Properties: In Torsion, 2008, 4 pages.

Corr, "Biomechanical behavior of scar tissue and uninjured skin in a porcine model", Wound Repair and Regeneration, Mar./Apr. 2009, vol. 17, No. 2, pp. 250-259.

Falk, "Seeing the Light", "Optics in Nature, Photography, Color, Vision, and Holography" 53-56 (1986).

Manschot,"The Measurement and Modelling of the Meachanical Properties of Human Skin In Vivo—I. The Measurement", Journal of Biomechanics, 1986, vol. 19. No. 7, pp. 511-515.

Satas, Handbook of Pressure Sensitive Adhesive Technology, Second Edition, (1989).

Stark, "Directional Variations in the Extensibility of Human Skin", British Journal of Plastic Surgery, Apr. 1977, vol. 30, No. 2, pp. 105-114.

Tegaderm CHG, Innovative Transparent Gel Pad, 2012, 1 page.

The Cutting Edge of Innovation, The story behind the development of 3M™ Ioban™ Antimicrobial Incise Drapes, 2012, 2 pages.

3M™ Tegaderm™ Transparent Film Dressing Frame Style 1624W, 2012, 2 pages.

3M™ Tegasorb™ Hydrolloid Dressing, 90001, 2006, 1 page.

3M™ Tegaderm™ Hydrocolloid Dressing, 90002, 2012, 2 pages.

3M™ Tegaderm™ Hydrocolloid Dressing 90003, 2012, 2 pages.

International Search Report for PCT/US2009/054662, mailed Oct. 6, 2009, 3 pages.

International Search Report for PCT/US2010/045956, mailed Oct. 20, 2010, 3 pages.

International Search Report for PCT/US2010/045958, mailed Jan. 19, 2011, 6 pages.

Written Opinion for PCT/US2009/054662, mailed Oct. 6, 2009, 10 pages.

Written Opinion for PCT/US2010,045956, Oct. 20, 2010, 7 pages.

Written Opinion for PCT/US2010,045958, Jan. 19, 2011, 10 pages.

* cited by examiner

US 8,758,237 B2

METHODS AND PRODUCTS FOR ILLUMINATING TISSUE

CROSS REFERENCE TO RELATED APPLICATIONS

This application is a national stage filing under 35 U.S.C. 371 of PCT/US2010/045956, filed Aug. 19, 2010, which claims priority to U.S. Provisional Application Ser. No. 61/236,027, filed Aug. 21, 2009, the disclosure of which is incorporated by reference in its entirety herein.

BACKGROUND

Surgical incise drapes are adhesive-coated organic polymeric drapes that are applied to the patient's skin typically after applying a presurgical preparation. The practitioner makes the incision right through the drape. In this manner, on the skin surface and the incisional site, the drape physically restricts the migration of bacteria remaining after the surgical prep procedure. The incise drape provides the surgeon a sterile surface adjacent to the wound. In addition, the incise drape may be used to hold other drapes securely on the patient. Surgical incise drapes used during such surgeries have been designed to be very thin and conformable and to have high adherence to the skin so as to allow surgical skin refraction with little or no lifting of the drape along the incisional edges.

Surgical wounds can be deep and cavernous. This can make it very difficult for the surgeon to visualize the tissue. Overhead lighting can illuminate the tissue but only to a certain degree and this is often blocked by the surgeon or scrub nurse. There is a need in such surgeries for improved illumination of the tissue in and around the incision as well as illuminating the tissue of a patient in other situations (e.g., placement of an intravenous (IV) line, visualization of the IV site, etc.).

SUMMARY

The present invention is directed to medical articles capable of illuminating the tissue of a patient. Such products include a conformable polymeric layer (e.g., a viscoelastic layer) and can be used in a surgical procedure (e.g., as part of an incise drape, or separately with a conventional an incise drape) or in various other medical applications.

In one embodiment, the present invention provides a medical article comprising: a flexible polymeric film having opposite first and second major surfaces; a viscoelastic lightguide layer disposed on a major surface of the film; and a light source optically coupled to the viscoelastic lightguide layer, wherein light emitted by the light source enters the viscoelastic lightguide layer and is transported within the viscoelastic lightguide layer by total internal reflection; and wherein the medical article is sterilized or sterilizable (e.g., by heat, sterilizing gas such as ethylene oxide, hydrogen peroxide; or other radiation techniques such as X-ray, gamma ray, electron beams, etc.), and conformable to a body part of a patient.

A medical article of the present invention may be adhered to the skin of a patient for illumination of tissue (e.g., the skin and underlying tissue, basal cell carcinoma, arteries or veins, or traumatized tissue such as surgical and chronic wounds).

In one embodiment, the medical article includes: a flexible polymeric film having opposite first and second major surfaces; a viscoelastic layer disposed on a major surface of the film; a light source; and a lightguide, wherein light emitted by the light source enters the lightguide and is transported within the lightguide by total internal reflection; wherein the medical article is adhered to the skin of the patient sufficiently for the skin to function as an extractor of the light. Alternatively, a presurgical skin preparation and/or polymer barrier film could be used directly on the skin in which case the medical article is adhered to the presurgical skin preparation. Such skin preparations could be formulated to facilitate extraction of light (or retard it).

In another embodiment, the medical article includes: a flexible polymeric film having opposite first and second major surfaces; a conformable polymeric layer disposed on a major surface of the film; a light source; and a lightguide, wherein light emitted by the light source enters the lightguide and is transported within the lightguide by total internal reflection; wherein the medical article is adhered to the patient. The conformable polymeric layer may be viscoelastic or elastic.

In certain embodiments, the viscoelastic layer (e.g., viscoelastic lightguide layer) comprises a (meth)acrylate, a rubber (synthetic or natural), a silicone, a polyurethane, a polyester, a polyurea, a polyamide (e.g., polyether amides such as PEBAX), a polyolefin (e.g., a metallocene polyolefin, polyisobutylene, butyl rubber), or combinations thereof (blends, copolymers, laminates thereof). In certain embodiments, the viscoelastic layer (e.g., viscoelastic lightguide layer) comprises a pressure sensitive adhesive. Suitable pressure sensitive adhesives include a natural rubber, a synthetic rubber, a styrene block copolymer, a (meth)acrylic block copolymer, a poly(meth)acrylate (e.g., a (meth)acrylate random copolymer, (meth)acrylate copolymers with other monomers), a polyvinyl ether, a polyolefin, or combinations thereof.

The present invention also provides methods of using the medical articles (e.g., incise drapes that include a conformable polymeric lightguide layer) described herein.

In one embodiment, the present invention provides a method of illuminating tissue of a patient during a surgical procedure. The method includes: providing an incise drape comprising: a conformable polymeric (e.g., viscoelastic) lightguide layer having opposite first and second major surfaces; and a light source optically coupled to the conformable polymeric lightguide layer; wherein light emitted by the light source enters the conformable polymeric lightguide layer and is transported within the conformable polymeric lightguide layer by total internal reflection; adhering the incise drape to the patient such that it conforms to the shape of the tissue of the patient; making an incision through the incise drape into the tissue to form a cut edge of the incise drape from which light is emitted at the cut edge; and retracting the tissue and incise drape along the incision in a manner such that the light emitted from the cut edge of the incise drape illuminates the tissue in and around the incision.

In another embodiment, the present invention provides a method of illuminating tissue of a patient. The method includes: providing a medical article comprising: a conformable polymeric lightguide layer having opposite first and second major surfaces; and a light source optically coupled to the conformable polymeric lightguide layer; wherein light emitted by the light source enters the conformable polymeric lightguide layer and is transported within the conformable polymeric lightguide layer by total internal reflection; adhering the medical article to the patient such that it conforms to the shape of the tissue of the patient and illuminates the tissue of the patient using light emitted from a major surface and/or an edge of the medical article. Preferably, the light is emitted from an edge of the medical article.

In yet another embodiment, the present invention provides a method of indicating excessive tissue bending during a surgical procedure. The method includes: providing an incise drape comprising: a conformable polymeric lightguide layer having opposite first and second major surfaces, and a light source, wherein light emitted by the light source enters the conformable polymeric lightguide layer and is transported within the conformable polymeric lightguide layer by total internal reflection; adhering the incise drape to the patient such that it conforms to the shape of the tissue of the patient; making an incision through the incise drape into the tissue to form a cut edge of the incise drape from which light is emitted at the cut edge; and retracting the tissue and incise drape along the incision causing the tissue adjacent to the incision to wrinkle; wherein the tissue wrinkling causes the total internal reflection angle of the lightguide to be exceeded, causing light emitted from the cut edge to be reduced and light emitted from a major surface of the incise drape along the wrinkled area to be increased, thereby indicating that excessive tissue bending may be occurring in the tissue in and around the incision.

By "optically coupling" it is meant that light from the light source can be directed at the lightguide in order to allow much of the light to enter the lightguide and be transported by total internal reflection, whether it is directly contacting (e.g., touching, incorporated within) the lightguide or not. Typically, at least 25% of the light from the light source will enter the lightguide. Preferably, at least 75% of the light from the light source will enter the lightguide.

By "illuminating" it is meant that UV, visible, or IR radiation has been directed at a target whether it is visible to the human eye or not. Thus, herein, the illumination of tissue can include heating it by IR radiation even though it cannot be seen.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a viscoelastic layer comprising a active agent can be interpreted to mean that the viscoelastic layer includes "one or more" active agents.

As used herein, the term "or" is generally employed in its usual sense including "and/or" unless the content clearly dictates otherwise.

The term "and/or" means one or all of the listed elements or a combination of any two or more of the listed elements (e.g., preventing and/or treating an affliction means preventing, treating, or both treating and preventing further afflictions).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
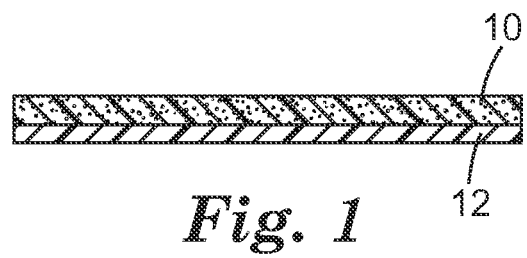
FIG. 1 is a cross-section of a conformable polymeric layer disposed on a release liner.

The present invention is directed to methods and products for illuminating the tissue of a patient. They include a conformable polymeric layer. Such products can be useful in a surgical procedure or in various other medical applications (e.g., viewing veins and arteries through the skin of a patient, heating tissue, etc.).

Similar designs of optical articles for use in various applications are described in U.S. Provisional Application No. 61/079,639 filed on Jul. 10, 2008, U.S. Provisional Application No. 61/114,865 filed on Nov. 14, 2008, and U.S. Provisional Application No. 61/169,973 filed on Apr. 16, 2009, as well as PCT Application No. US2009/046097 filed on Jun. 3, 2009, published as PCT Publication No. WO2010/005655; and U.S. Provisional Application No. 61/087,387 filed on Aug. 8, 2008, and U.S. Provisional Application No. 61/114, 849 filed on Nov. 14, 2008, and PCT Application No. US2009/052198 filed on Jul. 30, 2009, published as PCT Publication No. WO2010/017087.

The medical articles disclosed herein include a light source that emits light, a conformable polymeric layer (e.g., a viscoelastic layer), and a lightguide (which may be the same as the conformable polymeric (e.g., viscoelastic) layer) to manage the light. A conformable polymeric (e.g., viscoelastic) lightguide is desirable because it is generally soft and compliant such that the light source may be easily coupled to the lightguide so that light can enter the lightguide.

In some embodiments, the conformable polymeric (e.g., viscoelastic) lightguide comprises a pressure sensitive adhesive (PSA) which is generally tacky at room temperature. The light source may then be coupled to the conformable polymeric (e.g., viscoelastic) lightguide such that it is adhered to the lightguide. This may facilitate assembly of the medical article itself or constructions in which the device is used.

Light is typically extracted from the lightguide (e.g., viscoelastic lightguide) at one or more desired locations or areas of the lightguide including across an entire major surface of the lightguide. In some embodiments, an extractor may be used to extract light from the conformable polymeric (e.g., viscoelastic) lightguide. Again, due to the soft and compliant properties of the conformable polymeric (e.g., viscoelastic) lightguide, the extractor may be easily coupled to the lightguide so that light can enter the lightguide. If the conformable polymeric (e.g., viscoelastic) lightguide comprises a PSA, the extractor can be directly adhered to the lightguide without the need for additional materials to bond the two together.

The medical article may be used to provide light anywhere it is desired. For example, a medical article of the present invention may be adhered to the skin of a patient for illumination of tissue (e.g., the skin, underlying tissue as in a surgical incision, or veins). In one embodiment, the medical article includes: a flexible polymeric film having opposite first and second major surfaces; a conformable polymeric (e.g., viscoelastic) layer disposed on a major surface (e.g., the first major surface) of the film; a light source; and a lightguide, wherein light emitted by the light source enters the lightguide and is transported within the lightguide by total internal reflection; wherein the medical article is adhered to the patient. Adherence to the patient can be directly to the skin of the patient in a manner that the skin functions as an extractor of the light. Alternatively, adherence to the patient includes adherence to a presurgical skin preparation or barrier film on the skin of the patient.

In some embodiments described herein, the conformable polymeric (e.g., viscoelastic) layer is the lightguide, and light emitted by the light source enters the conformable polymeric (e.g., viscoelastic) lightguide and is transported within the lightguide by total internal reflection. In some embodiments, at least one surface of the conformable polymeric (e.g., viscoelastic) lightguide comprises a plurality of features oriented to extract light being transported within the conformable polymeric (e.g., viscoelastic) lightguide.

In some embodiments described herein, the conformable polymeric (e.g., viscoelastic) layer is disposed on the lightguide, and light emitted by the light source enters the lightguide and is transported within the lightguide by total internal reflection. In some embodiments, an interface formed between the lightguide and the conformable polymeric (e.g., viscoelastic) layer comprises a plurality of features oriented to extract light being transported within the lightguide.

The features can also come from the skin or they can be in the lightguide or the flexible polymeric film, for example. Such features cause the light to be extracted from the lightguide. As used herein, "emitted" light means that the light comes out on its own, whereas "extracted" light means that the light is perturbed by, for example, such features. Extraction requires a perturbation, once the perturbation occurs then emission occurs.

In one embodiment, the present invention provides a medical article comprising: a flexible polymeric film having opposite first and second major surfaces; a viscoelastic lightguide layer disposed on a major surface (e.g., the first major surface) of the film; and a light source optically coupled to the viscoelastic lightguide layer, wherein light emitted by the light source enters the viscoelastic lightguide layer and is transported within the viscoelastic lightguide layer by total internal reflection; and wherein the medical article is sterilized or sterilizable (e.g., by heat, sterilizing gas such as ethylene oxide, hydrogen peroxide; or other radiation techniques such as X-ray, gamma ray, electron beams, etc.), and conformable to a body part of a patient.

In certain embodiments, the medical article disclosed herein comprises a conformable polymeric (e.g., viscoelastic) lightguide layer and a light source. In certain embodiments, the medical article disclosed herein comprises a conformable polymeric (e.g., viscoelastic) layer separate from the lightguide, and a light source.

The conformable polymeric layer can be used with or without a flexible polymeric film, although using both is generally preferred. That is, for example, a conformable polymeric layer can be applied to the tissue (e.g., skin) of the patient, which is typically first treated with a presurgical skin preparation. Alternatively, a conformable polymeric layer can be applied to a flexible polymeric film, such as a conventional incise drape, which is typically first applied to the tissue of the patient after being treated with a presurgical skin preparation. Alternative methods of use of the conformable polymeric layer are also envisioned as further described herein.

The flexible polymeric film, the viscoelastic lightguide layer, or both may include a pressure sensitive adhesive disposed on at least a portion of at least one major surface thereof.

The conformable polymeric layer can be provided as a single layer 10 of a conformable polymeric (e.g., viscoelastic) material, which can be disposed on a release liner 12, for example, as shown in FIG. 1. A release liner may be on one or both major surfaces of the conformable polymeric layer. The conformable polymeric layer may be inherently tacky and/or it may include a layer of a pressure sensitive adhesive thereon. In preferred embodiments, this conformable polymeric layer is optically coupled with a light source and used as a lightguide.

Figure 2A:
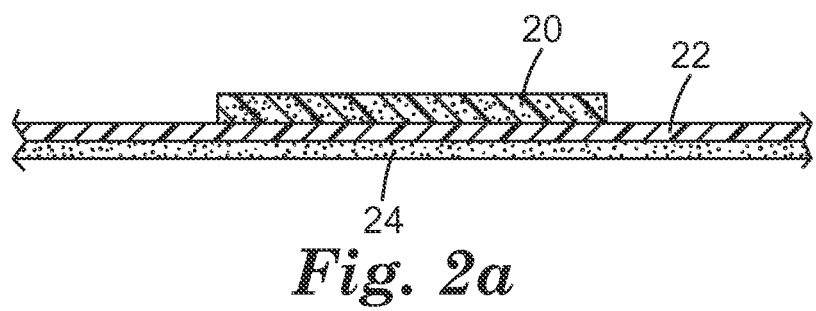
FIGS. 2a and 2b are cross-sections of two embodiments of a conformable polymeric layer disposed on a flexible polymeric film.

Alternatively, as shown in FIG. 2a, a flexible polymeric film and conformable polymeric layer can be provided as a composite in which the conformable polymeric layer 20 is disposed on (e.g., by coating or extruding) a surface of the flexible polymeric film 22. In this embodiment, the flexible polymeric film 22 may or may not include a layer of a pressure sensitive adhesive 24 on the surface of the flexible polymeric film 22 opposite that on which the conformable polymeric layer 20 is disposed. The embodiment shown in FIG. 2a would typically be applied to a patient using the pressure sensitive adhesive 24 resulting in the flexible polymeric film being disposed between the tissue of the patient and the conformable polymeric layer. Again, in preferred embodiments, this conformable polymeric layer is optically coupled with a light source and used as a lightguide.

Figure 2B:
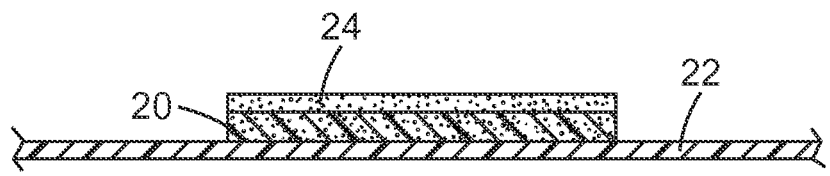

Or, as shown in FIG. 2b, a flexible polymeric film and conformable polymeric layer can be provided as a stress-distributing composite in which the conformable polymeric layer 20 is disposed on (e.g., by coating or extruding) a surface of the flexible polymeric film 22. In this embodiment, the conformable polymeric layer 20 may or may not include a layer of a pressure sensitive adhesive 24 on the surface of the conformable polymeric layer 20 opposite that on which the flexible polymeric film 22 is disposed. The embodiment shown in FIG. 2b would typically be applied to a patient using the pressure sensitive adhesive 24 resulting in the conformable polymeric layer being disposed between the tissue of the patient and the flexible polymeric film.

The conformable polymeric layer and flexible polymeric film of FIGS. 2a and 2b may be attached together directly (without any intervening materials) or through the use of a pressure sensitive adhesive, for example. They may be of the same size, or as shown in FIGS. 2a and 2b, the flexible polymeric film 22 may be larger in area than that of the conformable polymeric layer 20. In each of the figures presented herein, the relative sizes (e.g., thicknesses and lengths) of the layers/films are not necessarily in relative proportion.

Figure 3A:
FIGS. 3a and 3b are cross-sections of two embodiment of a conformable polymeric layer having a non-uniform thickness.
Figure 3B:

Although the conformable polymeric layer is shown in FIGS. 1, 2a, and 2b as having a uniform thickness (between the two major surfaces), the thickness may vary along the length of the material. For example, as shown in FIGS. 3a and 3b, the conformable polymeric layer may be thicker at the center and thinner (e.g., tapered as shown in FIG. 3a) at the edges. Certain advantages can be obtained when such non-uniform conformable polymeric layer is optically coupled with a light source and used as a lightguide.

For embodiments in which the conformable polymeric (e.g., viscoelastic) layer is the lightguide, light is emitted by the light source, enters the conformable polymeric (e.g., viscoelastic) lightguide, and propagates, reflects, and/or refracts according to the law of refraction and the principle of total internal reflection. The behavior of light within the conformable polymeric (e.g., viscoelastic) lightguide may depend on a variety of factors such as the surface structure of the lightguide, the presence (or absence) of additional substrate(s) in contact with the conformable polymeric (e.g., viscoelastic) lightguide, and/or the material compositions of the conformable polymeric (e.g., viscoelastic) lightguide and any additional substrate(s) in contact with the conformable polymeric (e.g., viscoelastic) lightguide. In addition, the behavior of light within the conformable polymeric (e.g., viscoelastic) lightguide may depend on the angular distribution of light that enters the lightguide.

A brief description of the law of refraction and total internal reflection is provided for the convenience of the reader. This brief description forms the basis for understanding the behavior of light with respect to the optical (medical) devices disclosed herein. For a detailed description of the behavior of light see, for example: "Seeing the Light" by D. S. Falk et al., John Wiley and Sons, Inc., 1986, pp. 53-56.

Figure 4A:
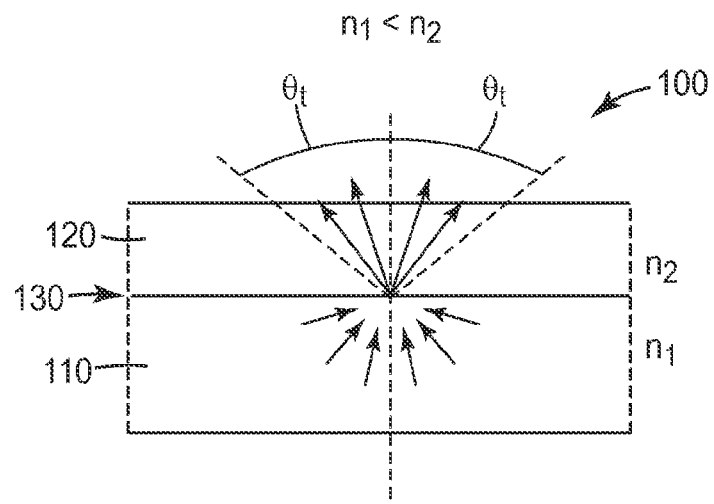
FIGS. 4a and 4b are schematic cross sections of layers illustrating principles of geometric optics.
Figure 4B:
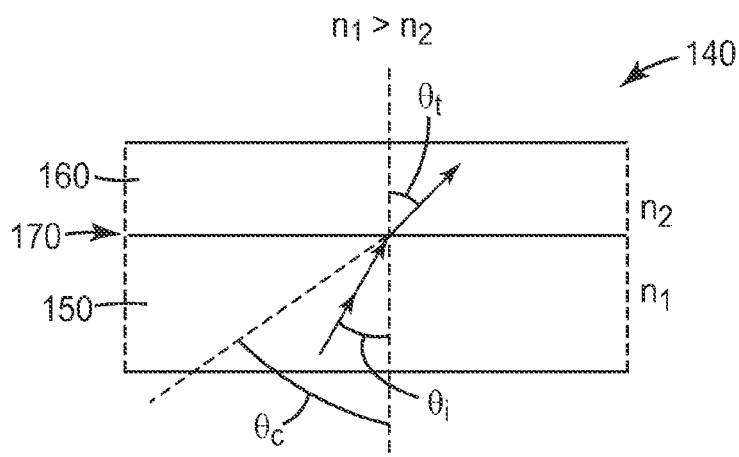

The law of refraction is illustrated in FIGS. 4a and 4b for a given pair of first and second layers. Light (represented by one or more rays for simplicity) propagates within the first layer and strikes the interface between the two layers. The light refracts, at a transmittance angle $\theta_t$, into the second layer according to the law of refraction:

$$\sin \theta_t = (n_1/n_2)(\sin \theta_i)$$

wherein $\theta_i$ is the incident angle, and $n_1$ and $n_2$ are the refractive indices of the first and second layers, respectively.

FIG. 4a shows a pair of layers 100 having first layer 110 and second layer 120 with refractive indices $n_1$ and $n_2$, respectively, such that $n_1 < n_2$. Light propagating within the first layer strikes interface 130 at many different incident angles and refracts into the second layer at angles within the transmittance angles $\theta_t$.

FIG. 4b shows a pair of layers 140 having first layer 150 and second layer 160 with refractive indices $n_1$ and $n_2$, respectively, such that $n_1 > n_2$. Light propagating within the first layer strikes interface 170 at incident angle $\theta_i$ and refracts at transmittance angle $\theta_t$ into the second layer according to the law of refraction. Only light having an incident angle less than or equal to critical angle $\theta_c$ will enter the second layer. All other light incident upon the interface is reflected. The critical angle $\theta_c$ is defined as:

$$\sin \theta_c = n_2/n_1$$

In general, total internal reflection occurs when light having a particular angular component or distribution is incident upon an interface at one or more angles greater than the critical angle $\theta_c$.

Figure 5:
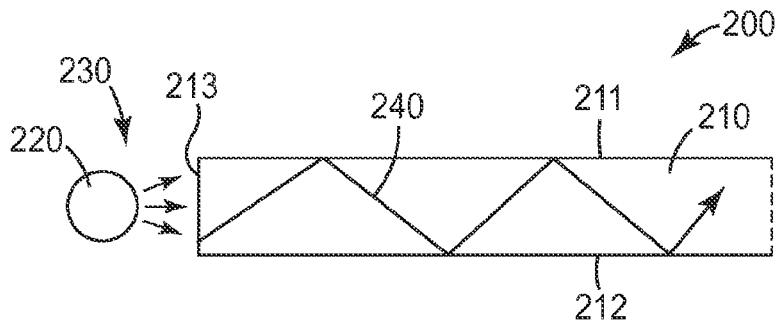
FIG. 5 shows a schematic cross-section of an exemplary medical article in which the conformable polymeric layer (e.g., viscoelastic layer) is the lightguide.

FIG. 5 shows an exemplary optical device 200. Light source 220 is positioned relative to viscoelastic lightguide 210 such that light emitted by the light source enters viscoelastic lightguide 210 and is transported within the layer by total internal reflection. Light emitted by the light source is represented by rays 230 which enter viscoelastic lightguide 210 through input surface 213 adapted to receive light from the light source, for example, at one or more edges of the lightguide. Light within the viscoelastic lightguide is represented by single ray 240 which is transported by total internal reflection. At least a portion of the viscoelastic lightguide has an optically smooth surface 211 and/or 212.

An optically smooth surface, as used herein, means that the surface is smooth enough such that light incident upon the surface is not affected undesirably by the surface. Preferably, this means that the surface has few defects, and more preferably is free of defects, wherein the defects have at least one dimension larger than the wavelength of the incident light. The optically smooth surface allows at least some of the light entering the conformable polymeric (e.g., viscoelastic) lightguide to be reflected at the surface such that this light continues to propagate within the layer according to the principle of total internal reflection.

In general, light propagating within the lightguide is either reflected or extracted from the lightguide. For reflection of light incident on an optically smooth surface, the observed reflection angle is within about 10° of the calculated reflection angle. Likewise, for refraction of light incident on an optically smooth surface, the observed transmittance angle is within about 10° of the calculated transmittance angle. Total internal reflection occurs if a predetermined amount, or at least within about 10% of a predetermined amount, of light does not escape the lightguide unless it is intentionally extracted from the lightguide.

In general, the surfaces of the lightguide may be unstructured as shown in FIG. 5, or they may have any three-dimensional structure depending on the desired effect. In general, a surface of the lightguide may comprise at least one feature that extends along a portion of the surface and is oriented to extract light from the lightguide. In some embodiments, the at least one feature comprises a plurality of features, the features comprising protrusions, depressions, or a combination thereof. Exemplary features comprise protrusions and/or depressions having lenticular, prismatic, ellipsoidal, conical, parabolic, pyramidal, square, rail, or rectangular shapes, or a combination thereof. Features comprising lenses are particularly useful for directing light to a preferred angular distribution. Exemplary features comprising linear prisms or elongated prisms are also particularly useful. Other exemplary features comprise protrusions and/or depressions having elongated, irregular, variably sloped lenticular, or random columnar shapes, or a combination thereof. Hybrids of any combination of shapes may be used, for example, elongated parabolic, pyramidal prismatic, rectangular-based prismatic, and rounded-tip prismatic shapes. The features may comprise random combinations of shapes.

Sizes of the features may be described by their overall shapes in three dimensions. In some embodiments, each feature may have a dimension of from about 1 to about 100 μm, for example, from about 5 to about 70 μm. A lightguide may have features that are all the same shape, but the sizes of the shapes may vary in at least one dimension. A lightguide may also have features that are different shapes, and the sizes of these features may or may not vary in any given dimension.

Surface structures of the features may also be varied. Surface structure of a feature generally refers to the sub-structure of the feature. Exemplary surface structures include optically smooth surfaces, irregular surfaces, patterned surfaces, or a combination thereof. For a lightguide having a plurality of features, each of the features may have the same surface structure. For a lightguide having a plurality of features, some of the features may have the same surface structure. For a lightguide having a plurality of features, each of the features may have a different surface structure. The surface structure of a feature may vary over portions of the feature.

An optically smooth surface of a feature may form part of the optically smooth surface of the lightguide. The optically smooth surfaces of the feature and the lightguide may be continuous or discontinuous with each other. If a plurality of features is used, the surfaces of some extracting features may be completely optically smooth or some may be partially optically smooth. The optically smooth surface may be in contact with an adjacent lightguide or substrate on which the lightguide is disposed.

The number of features, if used, for a given lightguide is at least one. A plurality of features, meaning at least two, may also be used. In general, any number of features may be included, e.g., 0, 1, 2, 3, 4 or 5 features; greater than 1, greater than 10, greater than 20, greater than 30, greater than 40, greater than 50, greater than 100, greater than 200, greater than 500, greater than 1000, or greater than 2000 features; or from about 1 to about 10, from about 1 to about 20, from about 1 to about 30, from about 1 to about 40, from about 1 to about 50, from about 1 to about 100, from about 1 to about 200, from about 1 to about 500, from about 1 to about 1000, or from about 1 to about 2000 features per unit area (e.g., per square centimeter).

The features may be randomly arranged, arranged in some type of regular pattern, or both. The distance between features may also vary. The features may be discreet or they may overlap. The features may be arranged in close proximity to one another, in substantial contact with each other, immediately adjacent each other, or some combination thereof. A useful distance between features is up to about 10 μm, or from about 0.05 μm to about 10 μm. The features may be offset with respect to one another, angularly as well as transversely. The areal density of the features may change over the length, width, or both.

The features may be arranged to obtain a desired optical effect. The features may be arranged to extract light uniformly or as a gradient from the lightguide, to hide discrete light sources, or to reduce Moiré.

The features may be used to control the amount and/or direction of light extracted from the lightguide. This can be carried out generally by varying the shape, size, surface structure, and/or orientation of the features. If a plurality of features is used, then the number and/or arrangement of the features may be varied, as well as the orientation of the features relative to each other.

In general, one may determine theoretically how varying the orientation of each feature can affect the amount and distribution of light that may be extracted from the lightguide. This may be carried out using ray tracing techniques consistent with the law of refraction and the principle of total internal reflection.

The shape of a feature may change the angular component of light which can increase or decrease the amount of light extracted from the lightguide. This may be the case if light propagates by total internal reflection within the lightguide and strikes a surface of a feature at an angle less than, equal to, or greater than the critical angle for the lightguide and air and/or an adjacent substrate(s). The amount of light extracted from the lightguide may increase or decrease accordingly.

The size of a feature may be changed such that more or less light can reflect off a surface of the feature, thus increasing or decreasing the amount of light extracted from the lightguide.

The surface structure of a feature may be used to control the distribution of light that is extracted from the lightguide. Light having a particular angular distribution may strike a feature and be extracted uniformly and/or randomly from the lightguide. Light may also be extracted uniformly and in a pattern, or randomly and in a pattern.

Figure 6:
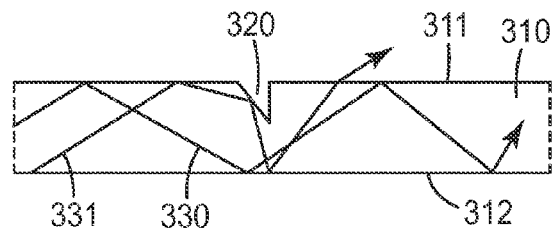
FIG. 6 shows a schematic cross-section of an exemplary conformable polymeric (e.g., viscoelastic) lightguide.

FIG. 6 shows a schematic cross section of exemplary viscoelastic lightguide 310 comprising feature 320. In this example, the feature is a notch-like depression of surface 311. Surfaces 311 and 312 are optically smooth surfaces. The surfaces of feature 320 are optically smooth surfaces. Exemplary behavior of light within viscoelastic lightguide 310 is shown by rays 330 and 331. Light represented by ray 330 propagates by total internal reflection within viscoelastic lightguide 310. Light represented by ray 331 propagates by total internal reflection within viscoelastic lightguide 310 and eventually strikes a surface of feature 320. As a result, the angular component of ray 331 is changed, and light represented by this ray can strike surface 312 at an angle less than the critical angle such that the light is extracted from viscoelastic lightguide 310. Thus, as exemplified in FIG. 6, the amount of light extracted from the viscoelastic lightguide may be increased. The direction in which light may be extracted from the viscoelastic lightguide may be varied by changing the orientation of feature 320 such that the angle at which ray 331 strikes the feature is increased or decreased but remains less than or equal to the critical angle.

Figure 7:
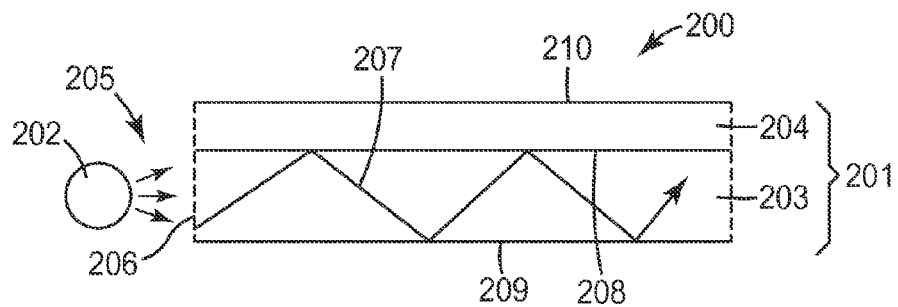
FIG. 7 shows a schematic cross-section of an exemplary medical article in which the conformable polymeric (e.g., viscoelastic) layer is distinct from the lightguide.

FIG. 7 shows an exemplary optical device 200 comprising medical article 201 and light source 202. Medical article 201 comprises viscoelastic layer 204 disposed on lightguide 203. Light source 202 is positioned relative to lightguide 203 such that light emitted by the light source enters the lightguide and is transported within the lightguide by total internal reflection. Light emitted by the light source is represented by rays 205 which enter lightguide 203 through input surface 206 adapted to receive light from the light source. Light within the lightguide is represented by single ray 207 which is transported by total internal reflection. At least a portion of the lightguide has an optically smooth surface 208 and/or 209. Viscoelastic layer 204 comprises upper surface 210.

Figure 8:
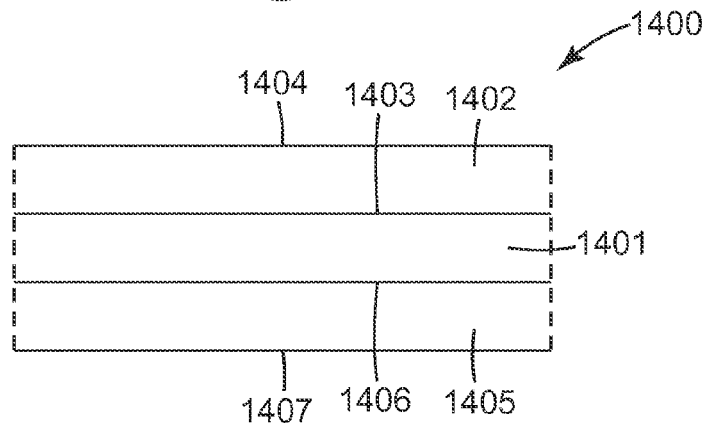
FIG. 8 shows a schematic cross-section of an exemplary medical article.

A conformable polymeric (e.g., viscoelastic) lightguide can be used in a variety of multilayer constructions depending on the particular application. Some of these embodiments are described below. In general, a conformable polymeric (e.g., viscoelastic) lightguide may be disposed on a substrate or between two substrates. Any one of the surfaces of the viscoelastic lightguide may be an interface formed between the lightguide and a substrate. For example, FIG. 8 shows a schematic cross-section of exemplary medical article 1400 comprising first substrate 1402 disposed on viscoelastic lightguide 1401; first interface 1403 formed between the two may be any one of the surfaces described above for the lightguide. Exemplary medical article 1400 also comprises optional second substrate 1405 disposed on viscoelastic lightguide 1401 opposite first substrate 1402; second interface 1406 formed between the two may be any one of the surfaces described above for the lightguide. Any of the surfaces of the viscoelastic lightguide may be used in combination for first interface 1403 and second interface 1406. Exemplary medical article 1400 also comprises first outer surface 1404 opposite first interface 1403, and second outer surface 1407 opposite second interface 1406. Any one of the surfaces of the viscoelastic lightguide may be first and/or second outer surfaces, 1404 and 1407, respectively. In general, any of the surfaces of the viscoelastic lightguide may be used in combination for first interface 1403, second interface 1406, first outer surface 1404 and second outer surface 1407.

The medical article is designed and arranged to control light in a predetermined way, for example, by light being extracted from the lightguide at one or more desired locations or areas. In general, the optically smooth surface may include the surface(s) of the extracting feature(s).

The medical article may also be used to provide "light on demand," e.g., the light source may be activated only under certain conditions The medical article may also be very adaptable, even by a user, so that it can be used in different lighting forms and constructions. For example, a viscoelastic lightguide may be provided in roll or sheet form such that it can be cut into various shapes and sizes. The light source may also be interchangeable with a viscoelastic lightguide, for example, if the light source should become unusable or if a different color of light is desired.

The amount and direction of light extracted from the lightguide may be controlled, at the very least, by the shape, size, number, arrangement, etc. of the features. In general, the viscoelastic lightguide can be designed such that light may be extracted from the lightguide in at least one predetermined direction, e.g., 1, 2, 3, 4, 5, 6, 7, 8, 9, 10, or more predetermined directions; from 1 to about 3 predetermined directions; from 1 to about 5 predetermined directions; from 1 to about 10 predetermined directions; or from 1 to about 100 predetermined directions.

The lightguide is generally in contact with at least one medium. The medium may comprise air or a substrate, particularly a flexible polymeric film as described herein and/or the skin of a patient. Particular substrates are described below for a variety of exemplary constructions.

The law of refraction and the principle of total internal reflection can be applied as described above to determine the amount of light extracted from the lightguide given a particular substrate directly in contact with the lightguide. For example, given a particular substrate in contact with the lightguide, the amount of light extracted from the lightguide and by the substrate may be less than about 0.5%, less than about 1%, less than about 2%, less than about 5%, less than about 10%, less than about 20%, less than about 30%, less than about 40%, less than about 50%, less than about 60%, less than about 70%, less than about 80%, or less than about 90% relative to the total amount of light that enters the lightguide. For another example, given a particular substrate in contact with the lightguide, the amount of light extracted from the lightguide by the substrate may be greater than about 10%, greater than about 20%, greater than about 30%, greater than about 40%, greater than about 50%, greater than about 60%, greater than about 70%, greater than about 80%, or greater than about 90% relative to the total amount of light that enters the lightguide. For yet another example, given a particular substrate in contact with the lightguide, the amount of light extracted from the lightguide may be from about 10 to about 50%, from about 20 to about 50%, from about 30 to about 50%, from about 50 to about 70%, from about 50 to about 80%, or from about 10 to about 90% relative to the total amount of light that enters the lightguide.

The law of refraction and the principle of total internal reflection can be applied as described above to determine the direction of light extracted from the lightguide given a particular substrate in contact with the lightguide. For example, given a particular substrate in contact with the lightguide, the transmittance angle for light extracted from the lightguide by the substrate may be determined for a given incident angle. For example, the transmittance angle for light extracted from the lightguide by the substrate may be from greater than about 5° to less than about 95°, greater than about 5° to less than about 60°, or greater than about 5° to less than about 30°.

The lightguide may have a refractive index greater than that of the substrate. The refractive index of the lightguide may be greater than about 0.002, greater than about 0.005, greater than about 0.01, greater than about 0.02, greater than about 0.03, greater than about 0.04, greater than about 0.05, greater than about 0.1, greater than about 0.2, greater than about 0.3, greater than about 0.4, or greater than about 0.5, as compared to the refractive index of the substrate.

The lightguide may have a refractive index less than that of the substrate. The refractive index of the lightguide may be less than about 0.002, less than about 0.005, less than about 0.01, less than about 0.02, less than about 0.03, less than about 0.04, less than about 0.05, less than about 0.1, less than about 0.2, less than about 0.3, less than about 0.4, or less than about 0.5, as compared to the refractive index of the substrate.

The lightguide and the substrate may have the same or nearly the same refractive index such that light can be extracted into the substrate with little or no change to the light. The refractive index difference of the lightguide and the substrate may be from about 0.001 to less than about 0.002.

The refractive index difference of the lightguide and the substrate may be from about 0.002 to about 0.5, from about 0.005 to about 0.5, from about 0.01 to about 0.5, from about 0.02 to about 0.5, from about 0.03 to about 0.5, from about 0.04 to about 0.5, from about 0.05 to about 0.5, from about 0.1 to about 0.5, from about 0.2 to about 0.5, from about 0.3 to about 0.5, or from about 0.4 to about 0.5.

Medical articles of the present invention may include a substrate that may be a reflector that reflects incident light being transported within the lightguide. In some embodiments, the reflector comprises a specular reflector wherein light propagating within the lightguide is reflected at a surface of the specular reflector according to the law of reflection. The law of reflection states that for light incident upon a surface and reflected by the surface, the reflection angle, $\theta_r$, is the same as or nearly the same as the incident angle, $\theta_i$, wherein both angles are defined relative to a plane of the surface. For a specular reflector, the reflection angle of light is within about 16° of the incident angle. A specular reflector may be fully or near fully specular as a reflector over some range of incident angles. Also, specular reflectors may be from about 85 to about 100% reflective, from about 90 to about 100%, or from about 95 to about 100%, across a particular region of the electromagnetic spectrum, for example, the visible region.

Suitable specular reflectors include mirrors such as a plane mirrors comprising a film of reflecting material, typically a metal, coated on glass. Suitable reflectors include mirrors that are multilayer optical films. Useful multilayer optical films comprise films having from about 10 to about 10,000 alternating layers of first and second polymer layers wherein the polymer layers comprise polyesters. Exemplary multilayer optical films are described in U.S. Pat. Nos. 5,825,543; 5,828,488 (Ouderkirk et al.); U.S. Pat. Nos. 5,867,316; 5,882,774; 6,179,948 B1 (Merrill et al.); U.S. Pat. Nos. 6,352,761 B1; 6,368,699 B1; 6,927,900 B2; 6,827,886 (Neavin et al.); U.S. Pat. No. 6,972,813 B1 (Toyooka); and U.S. Pat. No. 6,991,695; and U.S. Patent Application Publication Nos. 2006/0084780 A1 (Hebrink et al.); 2006/0216524 A1; 2006/0226561 A1 (Merrill et al.); and 2007/0047080 A1 (Stover et al.); as well as PCT Publication Nos. WO 95/17303; WO 95/17691; WO 95/17692; WO 95/17699; WO 96/19347; WO 97/01440; WO 99/36248; and WO 99/36262.

Exemplary specular reflectors include those available from 3M Company, for example, 3M High Intensity Grade Reflective Products such as High Reflective Visible Mirror Film and High Transmission Mirror Film, and VIKUITI films such as VIKUITI Enhanced Specular Reflector.

In some embodiments, the reflector comprises a diffuse reflector wherein light propagating within the viscoelastic lightguide is reflected and scattered at a surface of the diffuse reflector. For a diffuse reflector, light of a given incident angle reflects with multiple reflection angles wherein at least some of the reflection angles are greater than about 16° of the incident angle. A diffuse reflector may be fully or near fully reflective over some range of incident angles. Also, diffuse reflectors may be from about 85 to about 100% reflective, from about 90 to about 100%, or from about 95 to about 100%, across a particular region of the electromagnetic spectrum, for example, the visible region.

A diffuse reflector may comprise an irregular surface with respect to the wavelength of light being reflected. Light may be reflected at the surface. The diffuse reflector may comprise a layer of organic, inorganic or hybrid organic/inorganic particles disposed on a substrate. The particles may have a diameter of from greater than about 0.01 to about 100 μm, from greater than about 0.05 to about 100 μm, or from greater than about 0.05 to about 50 μm. The particles may be polymeric particles, glass beads, inorganic particles, metal oxide particles, or hybrid organic/inorganic particles. The particles may be solid, porous, or hollow. The particles may comprise microspheres having a polymeric shell with a blowing agent such as isobutene or isopentane inside the shell, for example, microspheres available as EXPANCEL microspheres from Expancel Co. The particles may be dispersed in a polymeric material or binder. Binders include one or more polymers and may be, for example, any of the viscoelastic materials and adhesive materials (cold seal adhesives, etc.) described above. The binder may comprise a PSA. The binder and particles may be coated onto a substrate such that the thickness of the binder is greater than, less than or about the same as the diameter of the particles. The substrate may comprise a polymer, metal, specular reflector, and the like.

For example, the diffuse reflector may comprise a layer of barium sulfate particles loaded in a polyethylene terephthalate film. Other constructions that provide a reflective surface are described in U.S. Pat. No. 7,481,563 (David et al.). Another example of a diffusely reflecting film with reflectivity of 95% is 3M Light Enhancement Film, Product No. 3635-100.

In some embodiments, the binder is light transmissive such that at least some of the light incident upon the layer enters the layer and becomes diffused. This diffused light is reflected upon being incident on a substrate that is a reflector. The diffusive material may comprise particles dispersed in a binder as described above. The refractive indices of the particles and binder may be different. For example, the refractive indices of the particles and binder may differ from about 0.002 to about 1, or from about 0.01 to about 0.5. This type of diffuse reflector may be from about 85 to about 100% reflective, from about 90 to about 100%, or from about 95 to about 100%, across a particular region of the electromagnetic spectrum, for example, the visible region. Exemplary light diffusing materials are described in U.S. Pat. No. 6,288,172 B1 (Goetz et al.). For example, the particles may comprise hollow glass spheres having a mean diameter of about 18 μm (SPHERICEL Grade 60P18 from Potters Industries Inc.), and the binder may comprise a PSA such as a silicone PSA.

In some embodiments, the medical article may include a multilayer optical film. Multilayer optical films can include mirrors as described above. Other types of multilayer optical films may also be used, for example, the multilayer optical film may be a reflective film, a polarizer film, a reflective polarizer film, a diffuse blend reflective polarizer film, a diffuser film, a brightness enhancing film, a turning film, a mirror film, or a combination thereof. Exemplary multilayer optical films include 3M VIKUITI films available from 3M Company. Exemplary multilayer optical films are described in the references cited above for multilayer optical films that are mirrors.

Conformable Polymeric Layer

A wide variety of conformable polymeric materials can be used in the conformable polymeric layers of the medical articles described herein. For example, a purely elastic material (i.e., an elastomer) is suitable as are viscoelastic materials. Such materials can be thermoplastic or thermoset. Preferably, they are optically clear (transparent or translucent), and more preferably, optically transparent.

For certain embodiments, preferred materials are viscoelastic. The viscoelastic layer (e.g., viscoelastic lightguide layer) comprises one or more viscoelastic materials. In general, viscoelastic materials exhibit both elastic and viscous behavior when undergoing deformation. Elastic characteristics refer to the ability of a material to return to its original shape after a transient load is removed. One measure of elasticity for a material is referred to as the tensile set value which is a function of the elongation remaining after the material has been stretched and subsequently allowed to recover (destretch) under the same conditions by which it was stretched. If a material has a tensile set value of 0%, then it has returned to its original length upon relaxation, whereas if the tensile set value is 100%, then the material is twice its original length upon relaxation. Tensile set values may be measured using ASTM D412. Useful viscoelastic materials may have tensile set values of greater than about 10%, greater than about 30%, or greater than about 50%; or from about 5 to about 70%, from about 10 to about 70%, from about 30 to about 70%, or from about 10 to about 60%.

Viscous materials that are Newtonian liquids have viscous characteristics that obey Newton's law which states that stress increases linearly with shear gradient. A liquid does not recover its shape as the shear gradient is removed. Viscous characteristics of useful viscoelastic materials include flowability of the material under reasonable temperatures such that the material does not decompose.

The viscoelastic material (e.g., viscoelastic lightguide) may have properties that facilitate sufficient contact or wetting with at least a portion of a substrate (e.g., skin of a patient) such that the viscoelastic component and the substrate are optically coupled. Light can then be extracted out of the viscoelastic component and into the substrate. The viscoelastic component is generally soft, compliant, and flexible. Thus, the viscoelastic component may have an elastic modulus (or storage modulus G') such that sufficient contact can be obtained, and a viscous modulus (or loss modulus G") such that the layer doesn't flow undesirably, and a damping coefficient (G"/G', tan D) for the relative degree of damping of the layer.

Useful viscoelastic materials may have a storage modulus, G', of less than about 300,000 Pa, measured at 10 rad/sec and a temperature of from about 20 to about 22° C. Useful viscoelastic materials may have a storage modulus, G', of from about 30 to about 300,000 Pa, measured at 10 rad/sec and a temperature of from about 20 to about 22° C. Useful viscoelastic materials may have a storage modulus, G', of from about 30 to about 150,000 Pa, measured at 10 rad/sec and a temperature of from about 20 to about 22° C. Useful viscoelastic materials may have a storage modulus, G', of from about 30 to about 30,000 Pa, measured at 10 rad/sec and a temperature of from about 20 to about 22° C. Useful viscoelastic materials may have a storage modulus, G', of from about 30 to about 150,000 Pa, measured at 10 rad/sec and a temperature of from about 20 to about 22° C., and a loss tangent (tan d) of from about 0.4 to about 3. Viscoelastic properties of materials can be measured using Dynamic Mechanical Analysis according to, for example, ASTM D4065, D4440, and D5279.

In some embodiments, the viscoelastic (e.g., viscoelastic lightguide) component comprises a PSA layer as described in the Dalquist criterion line (as described in Handbook of Pressure Sensitive Adhesive Technology, Second Ed., D. Satas, ed., Van Nostrand Reinhold, New York, 1989).

The viscoelastic (e.g., viscoelastic lightguide) component may have a particular peel force or at least exhibit a peel force within a particular range. For example, the viscoelastic component may have a 90° peel force of from about 50 to about 3000 g/in, from about 300 to about 3000 g/in, or from about 500 to about 3000 g/in. Peel force may be measured using a peel tester from IMASS.

In some embodiments, the viscoelastic (e.g., viscoelastic lightguide) component comprises an optically clear material having high light transmittance of from about 80 to about 100%, from about 90 to about 100%, from about 95 to about 100%, or from about 98 to about 100% over at least a portion of the visible light spectrum (about 400 to about 700 nm). In some embodiments, the viscoelastic (e.g., viscoelastic lightguide) component has a haze value of less than about 5%, less than about 3%, or less than about 1%. In some embodiments, the viscoelastic has a haze value of from about 0.01 to less than about 5%, from about 0.01 to less than about 3%, or from about 0.01 to less than about 1%. Haze values in transmission can be determined using a haze meter according to ASTM D1003.

In some embodiments, the viscoelastic (e.g., viscoelastic lightguide) component comprises an optically clear material having high light transmittance and a low haze value. High light transmittance may be from about 90 to about 100%, from about 95 to about 100%, or from about 99 to about 100% over at least a portion of the visible light spectrum (about 400 to about 700 nm), and haze values may be from about 0.01 to less than about 5%, from about 0.01 to less than about 3%, or from about 0.01 to less than about 1%. The viscoelastic component may also have a light transmittance of from about 50 to about 100%.

In some embodiments, the viscoelastic (e.g., viscoelastic lightguide) component is hazy and diffuses light, particularly visible light. A hazy viscoelastic component may have a haze value of greater than about 5%, greater than about 20%, or greater than about 50%. A hazy viscoelastic component may have a haze value of from about 5 to about 90%, from about 5 to about 50%, or from about 20 to about 50%.

In some embodiments, the viscoelastic (e.g., viscoelastic lightguide) component may be translucent in that it reflects and transmits light.

The viscoelastic (e.g., viscoelastic lightguide) component may have a refractive index in the range of from about 1.3 to about 2.6, 1.4 to about 1.7, or from about 1.5 to about 1.7. The particular refractive index or range of refractive indices selected for the viscoelastic may depend on the overall design of the optical device, e.g., the presence or absence of substrates in contact with the viscoelastic and the particular application in which the device may be used.

The viscoelastic (e.g., viscoelastic lightguide) component generally comprises at least one polymer. Suitable viscoelastic materials include a (meth)acrylate, a rubber (synthetic or natural), a silicone, a polyurethane, a polyester, a polyurea, a polyamide (e.g., polyether amides such as PEBAX), a polyolefin (e.g., a metallocene polyolefin, polyisobutylene, butyl rubber), or combinations thereof (blends, copolymers, or laminates thereof).

As stated above, for many applications elastomeric materials may be suitable. These can be thermoplastic (melt processable) or thermoset. Suitable elastomers include silicones such as addition cure, UV cure, and moisture curing silicones, polyurethanes, polyureas, polyacrylates, block copolymer polyacrylates, fluoroelastomers, perfluoroelastomers, polyether block amides, ethylene vinylaceate, and the like, as well as laminates and combinations thereof. Preferred such materials are optically clear.

In certain embodiments, the viscoelastic component may comprise at least one PSA. PSAs are useful for adhering together adherends and exhibit properties such as: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process. A quantitative description of PSAs can be found in the Dalquist reference cited above.

Useful PSAs include those based on natural rubbers, synthetic rubbers, styrene block copolymers, (meth)acrylic block copolymers, polyvinyl ethers, polyolefins, poly(meth)acrylates, and combinations thereof (blends, copolymers, or laminates thereof). As used herein, (meth)acrylic refers to both acrylic and methacrylic species and likewise for (meth)acrylate.

Useful PSAs include (meth)acrylates, rubbers, thermoplastic elastomers, silicones, urethanes, and combinations thereof. In some embodiments, the PSA is based on a (meth)acrylic PSA or at least one poly(meth)acrylate. Herein, (meth)acrylate refers to both acrylate and methacrylate groups. Particularly preferred poly(meth)acrylates are derived from: (A) at least one monoethylenically unsaturated alkyl (meth)acrylate monomer; and (B) at least one monoethylenically unsaturated free-radically copolymerizable reinforcing monomer. The reinforcing monomer has a homopolymer glass transition temperature (Tg) higher than that of the alkyl (meth)acrylate monomer and is one that increases the Tg and cohesive strength of the resultant copolymer. Herein, "copolymer" refers to polymers containing two or more different monomers, including terpolymers, tetrapolymers, etc.

Monomer A, which is a monoethylenically unsaturated alkyl (meth)acrylate, contributes to the flexibility and tack of the copolymer. Preferably, monomer A has a homopolymer Tg of no greater than about 0° C. Preferably, the alkyl group of the (meth)acrylate has an average of about 4 to about 20 carbon atoms, and more preferably, an average of about 4 to about 14 carbon atoms. The alkyl group can optionally contain oxygen atoms in the chain thereby forming ethers or alkoxy ethers, for example. Examples of monomer A include, but are not limited to, 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate. Benzyl acrylate may also be used. Other examples include, but are not limited to, poly-ethoxylated or -propoxylated methoxy (meth)acrylates such as acrylates of CARBOWAX (commercially available from Union Carbide) and NK ester AM90G (commercially available from Shin Nakamura Chemical, Ltd., Japan). Preferred monoethylenically unsaturated (meth)acrylates that can be used as monomer A include isooctyl acrylate, 2-ethyl-hexyl acrylate, and n-butyl acrylate. Combinations of various monomers categorized as an A monomer can be used to make the copolymer.

Monomer B, which is a monoethylenically unsaturated free-radically copolymerizable reinforcing monomer, increases the Tg and cohesive strength of the copolymer. Preferably, monomer B has a homopolymer Tg of at least about 10° C., for example, from about 10 to about 50° C. More preferably, monomer B is a reinforcing (meth)acrylic monomer, including an acrylic acid, a methacrylic acid, an acrylamide, or a (meth)acrylate. Examples of monomer B include, but are not limited to, acrylamides, such as acrylamide, methacrylamide, N-methyl acrylamide, N-ethyl acrylamide, N-hydroxyethyl acrylamide, diacetone acrylamide, N,N-dimethyl acrylamide, N,N-diethyl acrylamide, N-ethyl-N-aminoethyl acrylamide, N-ethyl-N-hydroxyethyl acrylamide, N,N-dihydroxyethyl acrylamide, t-butyl acrylamide, N,N-dimethylaminoethyl acrylamide, and N-octyl acrylamide. Other examples of monomer B include itaconic acid, crotonic acid, maleic acid, fumaric acid, 2,2-(diethoxy)ethyl acrylate, 2-hydroxyethyl acrylate or methacrylate, 3-hydroxypropyl acrylate or methacrylate, methyl methacrylate, isobornyl acrylate, 2-(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl formamide, N-vinyl acetamide, N-vinyl pyrrolidone, and N-vinyl caprolactam. Preferred reinforcing acrylic monomers that can be used as monomer B include acrylic acid and acrylamide. Combinations of various reinforcing monoethylenically unsaturated monomers categorized as a B monomer can be used to make the copolymer.

In some embodiments, the (meth)acrylate copolymer is formulated to have a resultant Tg of less than about 0° C. and more preferably, less than about −10° C. Such (meth)acrylate copolymers preferably include about 60 to about 98% by weight of at least one monomer A and about 2 to about 40% by weight of at least one monomer B, both relative to the total weight of the (meth)acrylate copolymer. Preferably, the (meth)acrylate copolymer has about 85 to about 98% by weight of at least one monomer A and about 2 to about 15% by weight of at least one monomer B, both relative to the total weight of the (meth)acrylate copolymer.

Useful rubber-based PSAs are generally of two classes, natural rubber-based or synthetic rubber-based. Useful natural rubber-based PSAs generally contain masticated natural rubber, for example, from about 20 to about 75% by weight of one or more tackifying resins, from about 25 to about 80% by weight of natural rubber, and typically from about 0.5 to about 2.0% by weight of one or more antioxidants, all relative to the total weight of the masticated rubber. Natural rubber may range in grade from a light pale crepe grade to a darker ribbed smoked sheet and includes such examples as CV-60, a controlled viscosity rubber grade and SMR-5, a ribbed smoked sheet rubber grade. Tackifying resins used with natural rubbers generally include but are not limited to wood rosin and its hydrogenated derivatives; terpene resins of various softening points, and petroleum-based resins, such as, the ESCOREZ 1300 series of C5 aliphatic olefin-derived resins from Exxon.

Antioxidants may be used with natural rubbers in order to retard oxidative attack on the rubber which can result in loss of cohesive strength of the adhesive. Useful antioxidants include but are not limited to amines, such as N—N'-di-beta-naphthyl-1,4-phenylenediamine, available as AGERITE Resin D from R.T. Vanderbilt Co., Inc.; phenolics, such as 2,5-di-(t-amyl)hydroquinone, available as SANTOVAR A, available from Monsanto Chemical Co.; tetrakis[methylene 3-(3',5'-di-tert-butyl-4'-hydroxyphenyl)propianate]methane, available as IRGANOX 1010 from Ciba-Geigy Corp.; 2,2'-methylenebis(4-methyl-6-tert-butyl phenol), known as Antioxidant 2246; and dithiocarbamates, such as zinc dithiodibutyl carbamate. Curing agents may be used to at least partially vulcanize (crosslink) the PSA.

Useful synthetic rubber-based PSAs include adhesives that are generally rubbery elastomers, which are either self-tacky or non-tacky and require tackifiers. Self-tacky synthetic rubber PSAs include, for example, butyl rubber, a copolymer of isobutylene with less than 3 percent isoprene, polyisobutylene, a homopolymer of isoprene, polybutadiene, or styrene/butadiene rubber. Butyl rubber PSAs often contain an antioxidant such as zinc dibutyl dithiocarbamate. Polyisobutylene PSAs do not usually contain antioxidants. Synthetic rubber PSAs, which generally require tackifiers, are also generally easier to melt process as compared to natural rubber PSAs which typically having very high molecular weights. They comprise polybutadiene or styrene/butadiene rubber, from 10 parts to 200 parts of a tackifier, and generally from 0.5 to 2.0 parts per 100 parts rubber of an antioxidant such as IRGANOX 1010. An example of a synthetic rubber is AMERIPOL 101 1A, a styrene/butadiene rubber available from BF Goodrich.

Tackifiers that may be used with synthetic rubber PSAs include derivatives of rosins such as FORAL 85, a stabilized rosin ester from Hercules, Inc.; the SNOWTACK series of gum rosins from Tenneco; the AQUATAC series of tall oil rosins from Sylvachem; synthetic hydrocarbon resins such as the PICCOLYTE A series, polyterpenes from Hercules, Inc.; the ESCOREZ 1300 series of C5 aliphatic olefin-derived resins; and the ESCOREZ 2000 Series of C9 aromatic/aliphatic olefin-derived resins. Curing agents may be added to at least partially vulcanize (crosslink) the PSA.

Useful thermoplastic elastomer PSAs include styrene block copolymer PSAs which generally comprise elastomers of the A-B or A-B-A type, where A represents a thermoplastic polystyrene block and B represents a rubbery block of polyisoprene, polybutadiene, or poly(ethylene/butylene), and resins. Examples of the various block copolymers useful in block copolymer PSAs include linear, radial, star and tapered styrene-isoprene block copolymers such as KRATON D1107P, available from Shell Chemical Co., and EUROPRENE SOL TE 9110, available from EniChem Elastomers Americas, Inc.; linear styrene-(ethylene-butylene) block copolymers such as KRATON G1657, available from Shell Chemical Co.; linear styrene-(ethylene-propylene) block copolymers such as KRATON G1750X, available from Shell Chemical Co.; and linear, radial, and star styrene-butadiene block copolymers such as KRATON D1118X, available from Shell Chemical Co., and EUROPRENE SOL TE 6205, available from EniChem Elastomers Americas, Inc. The polystyrene blocks tend to form domains in the shape of spheroids, cylinders, or plates that causes the block copolymer PSAs to have two phase structures.

Resins that associate with the rubber phase may be used with thermoplastic elastomer PSAs if the elastomer itself is not tacky enough. Examples of rubber phase associating resins include aliphatic olefin-derived resins, such as the ESCOREZ 1300 series and the WINGTACK series, available from Goodyear; rosin esters, such as the FORAL series and the STAYBELITE Ester 10, both available from Hercules, Inc.; hydrogenated hydrocarbons, such as the ESCOREZ 5000 series, available from Exxon; polyterpenes, such as the PICCOLYTE A series; and terpene phenolic resins derived from petroleum or terpentine sources, such as PICCOFYN A100, available from Hercules, Inc.

Resins that associate with the thermoplastic phase may be used with thermoplastic elastomer PSAs if the elastomer is not stiff enough. Thermoplastic phase associating resins include polyaromatics, such as the PICCO 6000 series of aromatic hydrocarbon resins, available from Hercules, Inc.; coumarone-indene resins, such as the CUMAR series, available from Neville; and other high-solubility parameter resins derived from coal tar or petroleum and having softening points above about 85° C., such as the AMOCO 18 series of alphamethyl styrene resins, available from Amoco, PICCO-VAR 130 alkyl aromatic polyindene resin, available from Hercules, Inc., and the PICCOTEX series of alphamethyl styrene/vinyl toluene resins, available from Hercules.

Useful silicone PSAs include polydiorganosiloxanes and polydiorganosiloxane polyoxamides. Useful silicone PSAs include silicone-containing resins formed from a hyrosilylation reaction between one or more components having silicon-bonded hydrogen and aliphatic unsaturation. Examples of silicon-bonded hydrogen components include high molecular weight polydimethylsiloxane or polydimethyldiphenylsiloxane, and that contain residual silanol functionality (SiOH) on the ends of the polymer chain. Examples of aliphatic unsaturation components include siloxanes functionalized with two or more (meth)acrylate groups or block copolymers comprising polydiorganosiloxane soft segments and urea terminated hard segments. Hydrosilylation may be carried out using platinum catalysts.

Useful silicone PSAs may comprise a polymer or gum and an optional tackifying resin.

The tackifying resin is generally a three-dimensional silicate structure that is endcapped with trimethylsiloxy groups (OSiMe$_3$) and also contains some residual silanol functionality. Examples of tackifying resins include SR 545, from General Electric Co., Silicone Resins Division, Waterford, N.Y., and MQD-32-2 from Shin-Etsu Silicones of America, Inc., Torrance, Calif.

Manufacture of typical silicone PSAs is described in U.S. Pat. No. 2,736,721 (Dexter). Manufacture of silicone urea block copolymer PSAs is described in U.S. Pat. No. 5,214,119 (Leir, et al).

Useful silicone PSAs may also comprise a polydiorganosiloxane polyoxamide and an optional tackifier as described in U.S. Pat. No. 7,361,474 (Sherman et al.). For example, the polydiorganosiloxane polyoxamide may comprise at least two repeat units of Formula I:

where p is at least 2. G may comprise an alkylene, heteroalkylene, arylene, aralkylene, polydiorganosiloxane, or a combination thereof. The integer n may be an integer of 40 to 500. These polydiorganosiloxane polyoxamides can be used in combination with a tackifier. Useful tackifiers include silicone tackifying resins as described in U.S. Pat. No. 7,090,922 B2 (Zhou et al.). Some of these silicone-containing PSAs may be heat activated.

The PSA may be crosslinked to the extent that the crosslinks do not interfere with desired properties of the viscoelastic or elastic lightguide. Generally, the PSA may be crosslinked to the extent that the crosslinks do not interfere with the viscous characteristics of the viscoelastic. Crosslinking is used to build molecular weight and strength of the PSA. The degree of crosslinking may be selected based upon the application for which the viscoelastic is intended. Crosslinking agents may be used to form chemical crosslinks, physical crosslinks or a combination thereof. Chemical crosslinks include covalent bonds and ionic bonds. Covalent crosslinks may be formed by incorporating a multi-functional monomer in the polymerization process, followed by curing using, e.g., ultraviolet radiation, heat, ionizing radiation, moisture, or a combination thereof.

Physical crosslinks include noncovalent bonds and are generally thermally reversible. Examples of physical crosslinks include high Tg (i.e., those having a Tg higher than room temperature, preferably higher than 70° C.) polymer segments included, for example, in thermoplastic elastomer block copolymers. Such segments aggregate to form physical crosslinks that dissipate upon heating. If a physically crosslinked PSA is used such as a thermoplastic elastomer, the embossing typically is carried out at temperature below, or even substantially below, the temperature at which the adhesive flows. Hard segments include the styrene macromers of U.S. Pat. No. 4,554,324 (Husman et al.) and/or acid/base interactions (i.e., those involving functional groups within the same polymer or between polymers or between a polymer and an additive) such as polymeric ionic crosslinking as described in PCT Publication No. WO 99/42536 (Stark et al.).

Suitable crosslinking agents are also disclosed in U.S. Pat. No. 4,737,559 (Kellen), U.S. Pat. No. 5,506,279 (Babu et al.), and U.S. Pat. No. 6,083,856 (Joseph et al.). The crosslinking agent can be a photocrosslinking agent, which, upon exposure to ultraviolet radiation (e.g., radiation having a wavelength of from about 250 to about 400 nm), causes the copoly-

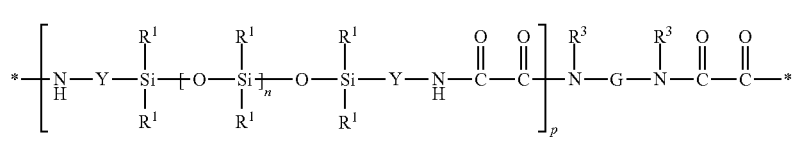

wherein: each R$^1$ is independently an alkyl, haloalkyl, aralkyl, alkenyl, aryl, or aryl substituted with an alkyl, alkoxy, or halo, wherein at least 50 percent of the R$^1$ groups are methyl; each Y is independently an alkylene, aralkylene, or a combination thereof; G is a divalent residue equal to a diamine of formula R$^3$HN-G-NHR$^3$ minus the two —NHR$^3$ groups; R$^3$ is hydrogen or alkyl or R$^3$ taken together with G and with the nitrogen to which they are both attached forms a heterocyclic group; n is independently an integer of 40 to 1500; and p is an integer of 1 to 10; and an asterisk (*) indicates a site of attachment of the repeat unit to another group in the copolymer. The copolymer may have a first repeat unit where p is equal to 1 and a second repeat unit mer to crosslink. The crosslinking agent is used in an effective amount, by which is meant an amount that is sufficient to cause crosslinking of the PSA to provide adequate cohesive strength to produce the desired final adhesion properties. Preferably, the crosslinking agent is used in an amount of about 0.1 part to about 10 parts by weight, based on the total weight of monomers.

In some embodiments, the viscoelastic (e.g., viscoelastic lightguide) comprises a PSA formed from a (meth)acrylate block copolymer as described in U.S. Pat. No. 7,255,920 B2 (Everaerts et al.). In general, these (meth)acrylate block copolymers comprise: at least two A block polymeric units that are the reaction product of a first monomer composition comprising an alkyl methacrylate, an aralkyl methacrylate, an aryl methacrylate, or a combination thereof, each A block having a Tg of at least 50° C., the methacrylate block copolymer comprising from 20 to 50 weight percent A block; and at least one B block polymeric unit that is the reaction product of a second monomer composition comprising an alkyl (meth) acrylate, a heteroalkyl (meth)acrylate, a vinyl ester, or a combination thereof, the B block having a Tg no greater than 20° C., the (meth)acrylate block copolymer comprising from 50 to 80 weight percent B block; wherein the A block polymeric units are present as nanodomains having an average size less than about 150 nm in a matrix of the B block polymeric units.

In some embodiments, the viscoelastic (e.g., viscoelastic lightguide) comprises a clear acrylic PSA, for example, those available as transfer tapes such as VHB Acrylic Tape 4910F from 3M Company and 3M Optically Clear Laminating Adhesives (8140 and 8180 series).

In some embodiments, the viscoelastic (e.g., viscoelastic lightguide) comprises a PSA formed from at least one monomer containing a substituted or an unsubstituted aromatic moiety as described in U.S. Pat. No. 6,663,978 B1 (Olson et al.):

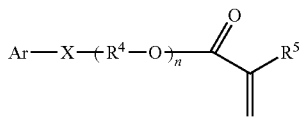

wherein Ar is an aromatic group which is unsubstituted or substituted with a substituent selected from the group consisting of $Br_y$ and $R^6_z$ wherein y represents the number of bromine substituents attached to the aromatic group and is an integer of from 0 to 3, $R^6$ is a straight or branched alkyl of from 2 to 12 carbons, and z represents the number of $R^6$ substituents attached to the aromatic ring and is either 0 or 1 provided that both y and z are not zero; X is either O or S; n is from 0 to 3; $R^4$ is an unsubstituted straight or branched alkyl linking group of from 2 to 12 carbons; and $R^5$ is either H or $CH_3$.

In some embodiments, the viscoelastic (e.g., viscoelastic lightguide) comprises a copolymer as described in U.S. Patent Application Publication No. 2009-0105437-A1 (Determan et al.), comprising (a) monomer units having pendant bephenyl groups and (b) alkyl (meth)acrylate monomer units.

In some embodiments, the viscoelastic (e.g., viscoelastic lightguide) comprises a copolymer as described in U.S. Provisional Application Ser. No. 60/983,735 (63760US002, Determan et al.), which is the priority document for PCT Publication No. WO2009/058513, comprising (a) monomer units having pendant carbazole groups and (b) alkyl (meth) acrylate monomer units.

In some embodiments, the viscoelastic (e.g., viscoelastic lightguide) comprises an adhesive as described in U.S. Provisional Application Ser. No. 60/986,298 (Schaffer et al.), which is the priority document for PCT Publication No. WO2009/061673, comprising a block copolymer dispersed in an adhesive matrix to form a Lewis acid-base pair. The block copolymer comprises an AB block copolymer, and the A block phase separates to form microdomains within the B block/adhesive matrix. For example, the adhesive matrix may comprise a copolymer of an alkyl (meth)acrylate and a (meth) acrylate having pendant acid functionality, and the block copolymer may comprise a styrene-acrylate copolymer. The microdomains may be large enough to forward scatter incident light, but not so large that they backscatter incident light. Typically these microdomains are larger than the wavelength of visible light (about 400 to about 700 nm). In some embodiments the microdomain size is from about 1.0 to about 10 µm.

The viscoelastic lightguide may comprise a stretch releasable PSA. Stretch releasable PSAs are PSAs that can be removed from a substrate if they are stretched at or nearly at a zero degree angle. In some embodiments, the viscoelastic lightguide or a stretch release PSA used in the viscoelastic lightguide has a shear storage modulus of less than about 10 MPa when measured at 1 rad/sec and −17° C., or from about 0.03 to about 10 MPa when measured at 1 rad/sec and −17° C. Stretch releasable PSAs may be used if disassembling, reworking, or recycling is desired.

The viscoelastic (e.g., viscoelastic lightguide) can optionally include one or more additives such as filler, particles, plasticizers, chain transfer agents, initiators, antioxidants, stabilizers, fire retardants, viscosity modifying agents, foaming agents, antistats, colorants such as dyes and pigments, fluorescent dyes and pigments, phosphorescent dyes and pigments, fibrous reinforcing agents, and woven and non-woven fabrics.

Such additives can be active agents (active for the desired effect). Preferably, the active agents incorporated into the conformable polymeric layer are soluble in the conformable polymeric layer. Alternatively, active agents can be disposed on (e.g., coated or printed) a surface of the medical articles described herein if they are not soluble in the conformable polymeric layer, for example.

Suitable active agents include, for example, antimicrobials (iodine or an iodophor and others as described herein with respect to the flexible polymeric film), anti-irritants, actives to promote wound healing (compounds which release nitric oxide, steroids, hormones, peptides, etc.), skin lighting agents (and other agents to reduce or eliminate age spots), analgesics such as ibuprofen, menthol, methyl salicylate, camphor and the like, or combinations thereof. Other suitable antimicrobial agents include include alpha-hydroxyacids, such as but not limited to lactic acid, malic acid, citric acid, 2-hydroxybutanoic acid, 3-hydroxybutanoic acid, mandelic acid, gluconic acid, tartaric acid, as well as derivatives thereof (e.g., compounds substituted with hydroxyls, phenyl groups, hydroxyphenyl groups, alkyl groups, halogens, as well as combinations thereof); betahydroxy acids such as salicylic acid, C8-C18 fatty acids; C8-C18 sulfonic acids and there salts; quaternary ammonium surfactants having at least one alkyl chain of at least 8 carbon atoms and/or a benzyl group; parachlorometaxylenol (PCMX); triclosan; hexachlorophene; fatty acid monoesters of glycerin and propylene glycol, such as but not limited to glycerol monolaurate, glycerol monocaprylate, glycerol monocaprate, propylene glycol monolaurate, propylene glycol monocaprylate, propylene glycol monocaprate; phenols; polyquaternary amines, such as but not limited to polyhexamethylene biguanide; quaternary ammonium surfactants having one or two alkyl groups of at least 8 carbon atoms such as benzalkonium chloride, cetyl pyridinium chloride, didecyldimethylammonium chloride and the like, small molecule cationic antimicrobials such as benzethonium halides and octenidine and derivatives thereof, quaternary ammonium silanes having at least one alkyl chain of at least 8 carbon atoms; silver and silver salts, such as but not limited to silver chloride, silver oxide, and silver sulfadiazine; methyl, ethyl, propyl, and butyl parabens; octenidene; compounds that generate hydrogen peroxide such as perborates, complexes of hydrogen peroxide with polyvinylpyrrolidone (e.g., Peroxydone from ISP), natural oils such as tea tree oil, grape fruit seed extract, and the like, as well as combinations thereof.

Depending on the material and its properties (e.g., modulus), the thickness of the conformable polymeric layer may vary. For certain embodiments, particularly when used in or with a surgical incise drape, the thickness of the conformable polymeric layer, which has opposite first and second major surfaces, is typically at least 1 millimeter (mm), and preferably at least 2 mm, between the first and second major surfaces. A conformable polymeric layer of greater than 2 mm is preferred. If the conformable polymeric layer is too thick, the practitioner may not be able to feel the underlying anatomy (e.g., bony prominences) for effective placement of the incision. Also, as the thickness of the conformable polymeric layer increases, its conformability over curved body surfaces typically decreases. The thickness of the conformable polymeric layer is typically no more than 10 mm, often no more than 8 mm, and even more often no more than 5 mm. An exemplary range of thicknesses is 3 mm to 5 mm.

The size of the conformable polymeric layer (e.g., viscoelastic lightguide layer) may be of a wide variety of sizes depending on the use (e.g., the size of the incision to be made). For example, when used in or with a surgical incise drape, a typical conformable polymeric layer is at least 2 cm longer on each end than the desired length of the incision. A typical conformable polymeric layer is at least 3 cm, and often no more than 4 cm, wide on each side of the incision (making a typical conformable polymeric layer 6 cm to 8 cm wide). Larger layers can be used if desired, however, for surgical applications such layers are typically wasteful and can be harder to apply.

The thickness of the conformable polymeric layer (e.g., viscoelastic layer) is typically uniform throughout. It can also be contoured or nonuniform, however, such that the thickness may vary throughout the material for desired effect (see, e.g., FIGS. 3a and 3b). For example, it may be thicker in and around the area for the incision (e.g., at the center of the material) and thinner over the remainder of the area (e.g., tapered at the edges of the material), which can result in more conformability at the edges. A tapered construction (as shown in FIG. 3a) may be desired in certain embodiments, particularly where the flexible polymeric material overlies the conformable polymeric layer, as the thinner edges result in less of a step at the edges. Also, a medical article in which the edges are thinner than the center can result in more light being directed into the center, particularly when light is coupled at more than one edge.

A release liner may be disposed on the conformable polymeric layer, whether used as a lightguide or not. The release liner can be removed at any time to expose the conformable polymeric layer. Exemplary release liners have a low adhesion surface for contact with the adhesive layer. Release liners may comprise paper such as Kraft paper, or polymeric films such as poly(vinyl chloride), polyester, polyolefin, cellulose acetate, ethylene vinyl acetate, polyurethane, and the like. The release liner may be coated with a layer of a release agent such as a silicone-containing material or a fluorocarbon-containing material. Exemplary release liners include liners commercially available from CP Films Inc. under the trade designations "T-30" and "T-10" that have a silicone release coating on polyethylene terephthalate film. Exemplary release liners include structured release liners such as those which are microstructured. For products intended for gamma sterilization, use of a paper, polyethylene, polyester, or polyethylene coated polyester liner is preferred.

Lightguide

If the medical articles herein include a lightguide other than the conformable polymeric layer (viscoelastic or elastic layer), the lightguide comprises an optically transmissive material, i.e., the lightguide comprises an optically transparent material capable of transmitting light. The refractive index of the lightguide may range from about 1.3 to about 2.6, 1.4 to about 1.7, or from about 1.5 to about 1.7. The particular material used to make the lightguide depends on the required refractive index or range or refractive indices as may be influenced by other design elements of the medical article. For example, the material used to make the lightguide may need to have a refractive index greater than that of the viscoelastic layer.

The lightguide may comprise polymeric material or glass (as in a viewing window in a dressing), or some combination thereof. Exemplary polymers that may be used for the lightguide include polycarbonates, poly(meth)acrylates, polystyrenes, polyurethanes, polyesters, polyimides, cyclic olefin copolymers. Particular polymers that may be used for the lightguide include polymethylmethacrylate, polyethyleneterephthalate, polyethylenenaphthalate, bis-phenol A polycarbonate, polystyrene, polyvinylacetate, and derivatives thereof. The lightguide may comprise a liquid (for example, if sealed in a chamber).

The lightguide may be made from melt-processed or radiation-cured materials.

The lightguide may be a film as described in U.S. patent application Ser. No. 12/199,862, published as U.S. Patent Application Publication No. US2009/0067151; U.S. Pat. No. 6,033,604 (Lundin et al.); U.S. Patent Application Publication No. 2003/0034445 A1 (Boyd et al.); PCT Publication No. WO 02/070237 A1 (Lundin); U.S. Patent Application Publication No. 2008/232135 A1 (Kinder et al.); U.S. Pat. No. 6,367,941 B2 (Lea et al.); U.S. Pat. No. 6,845,212 B2 (Gardiner et al.); PCT Publication No. WO 2008/022007 A1 (Vogt et al.); and U.S. Pat. No. 7,046,905 B1 (Gardiner et al.).

The thickness of the lightguide is not particularly limited as long as it can function as desired. The thickness of the lightguide may be selected based on or in conjunction with the light source. For example, design parameters may limit or even require that a particular light source(s) be used, and there may be a minimum amount, or range of amounts, of light that is required to enter the lightguide. Thus, the thickness of the lightguide may be selected so that the required amount of light from a given light source can enter the lightguide. A maximum thickness of the lightguide may be required for use in optical devices designed to be particularly thin. Exemplary thicknesses for the lightguide range from about 0.4 mil (10 microns) to about 1000 mil (25 mm), from about 1 mil (25 microns) to about 300 mil (7.5 mm), from about 1 mil (25 microns) to about 60 mil (1500 microns), or from about 0.5 mil (13 microns) to about 30 mil (750 microns).

Light Source

In general, the lightguide (e.g., viscoelastic or elastic lightguide) is adapted to receive at least some light emitted by the light source. In some embodiments, a specially designed input surface may not be needed because the light source can be pressed into the lightguide (e.g., viscoelastic or elastic conformable lightguide) such that optical coupling occurs. In some embodiments, the light source may stick to the lightguide, for example, if the lightguide is a viscoelastic lightguide comprising a PSA. In some embodiments, the light source may be embedded in the lightguide (e.g., viscoelastic lightguide). Thus, the light source may be optically coupled to the lightguide, whether it is directly coupled to (e.g., touching, incorporated within) the lightguide or not.

In some embodiments, the lightguide (e.g., viscoelastic lightguide) comprises an input surface adapted to receive light from the light source. The input surface may have a variety of topographies depending on the optical coupling means and/or the particular light source. The input surface may have an appropriate curvature. The input edge comprising the input surface may have a particular cavity, for example a concave hemispherical cavity, to receive a convex lens of a light source. Alternatively, the input surface may have refractive structures such as prisms or lenses to optically couple light from the light source into the lightguide (e.g., viscoelastic lightguide).

In some embodiments, an extractor article disposed between the light source and the input edge may be used to facilitate optical coupling with at least some of the light emitted by the light source. Useful extractor articles may have an appropriate curvature for extracting light from the light source. A coupling material for matching refractive indices of the lightguide (e.g., viscoelastic lightguide) and some element of the light source may be used. A crosslinkable material may be used for attaching the lightguide (e.g., viscoelastic lightguide) to some part of the light source, and subsequently cured using heat and/or light to form the crosslinked material. The crosslinkable material may be cured by light from the light source upon attachment.

The coupling material may comprise silicone gel. The silicone gel may be crosslinked. The silicone gel may be mixed with a silicone oil. The silicone gel may comprise one or more silicone materials such as, for example, dimethylsilicone, diphenylsilicone, or phenylmethylsilicone. The silicone gel may comprise phenylmethylsilicone moieties that are crosslinked. The silicone gel may comprise phenylmethylsilicone moieties which are crosslinked and phenylmethylsilicone oil. The silicone gel may comprise phenylmethylsilicone moieties which are crosslinked and phenylmethylsilicone oil in a weight ratio from 0.2:1 to 5:1. The silicone gel may comprise crosslinked phenylmethylsilicone. Exemplary use of silicone gels is described in U.S. Pat. No. 7,315,418 (DiZio et al.).

The light source may be optically coupled to the lightguide (e.g., viscoelastic lightguide) such that at least some of the light from the light source can enter the lightguide. For example, a light source may be optically coupled to the lightguide (e.g., viscoelastic lightguide) such that greater than 1, greater than 10, greater than 20, greater than 30, greater than 40, greater than 50, greater than 90%, or about 100% of light emitted by the light source enters the lightguide (e.g., viscoelastic or elastic lightguide). For another example, a light source may be optically coupled to the lightguide (e.g., viscoelastic lightguide) such that from about 1 to about 10%, from about 1 to about 20%, from about 1 to about 30%, from about 1 to about 40%, from about 1 to about 50%, from about 1 to about 100%, from about 1 to about 100%, from about 50 to about 100%, or from about 1 to about 100% of light emitted by the light source enters the lightguide (e.g., viscoelastic lightguide). The light source may emit light having a random or a particular angular distribution.

The light source may comprise any suitable light source. Exemplary light sources include linear light sources such as cold cathode fluorescent lamps and point light sources such as light emitting diode (LEDs). Exemplary light sources also include organic light-emitting devices (OLEDs), incandescent bulbs, fluorescent bulbs, halogen lamps, UV bulbs, infrared sources, near-infrared sources, lasers, or chemical light sources. In general, the light emitted by the light source may be visible or invisible. The light used in the medical articles and methods of the present invention may be of the VIS, UV, or IR wavelength. It may be of a narrow spectrum of wavelengths (e.g., a laser has more than one wavelength, an LED has a narrow spectrum of multiple wavelengths) or a broad spectrum of wavelengths (e.g., as emitted from a light bulb). The light source may be used for visual illumination or for other purposes such as heating (e.g., IR radiant heating, antimicrobial activity, or other purposes).

At least one light source may be used. For example, from 1 to about 10,000 light sources may be used. The light source may comprise a row of LEDs positioned at or near an edge of the lightguide (e.g., viscoelastic lightguide). The light source may comprise LEDs arranged on a circuit such that light emitted from the LEDs lights up continuously or uniformly the lightguide (e.g., viscoelastic lightguide) throughout a desired area. The light source may comprise LEDs that emit light of different colors such that the colors can mix within the lightguide (e.g., viscoelastic lightguide). In this way, a graphic could be designed to appear differently at different times during its use. Also, different colors may be turned on during different times during a procedure.

The light source may be powered by any suitable means. The light source may be powered using a battery (e.g., a thin film battery, battery tape), a DC power supply, an AC to DC power supply, an AC power supply, a solar photovoltaic cell, or wirelessly through RFID means as described in U.S. Provisional Application No. 61/256,827, filed on Oct. 30, 2009 entitled "Remotely Powered Lightguide."

The light source can be LEDs encapsulated into a solid material such as polycarbonate or polymethylmethacrylate (PMMA) formed with a pointed tip for injection and connected with a housing that utilizes industry standard electrical connection clips or connectors (e.g., as used in 3M RED DOT electrode products). In this way, LEDs could be pushed into a thick conformable polymeric (e.g., viscoelastic) lightguide layer at any desired point to give custom illumination to the desired site of the patient's tissue. Such LED "push pins" or "push strips" could be powered by a strip of battery tape applied over them. Alternately, push pins could be powered by a strip of battery tap through which they are inserted.

Figure 9:
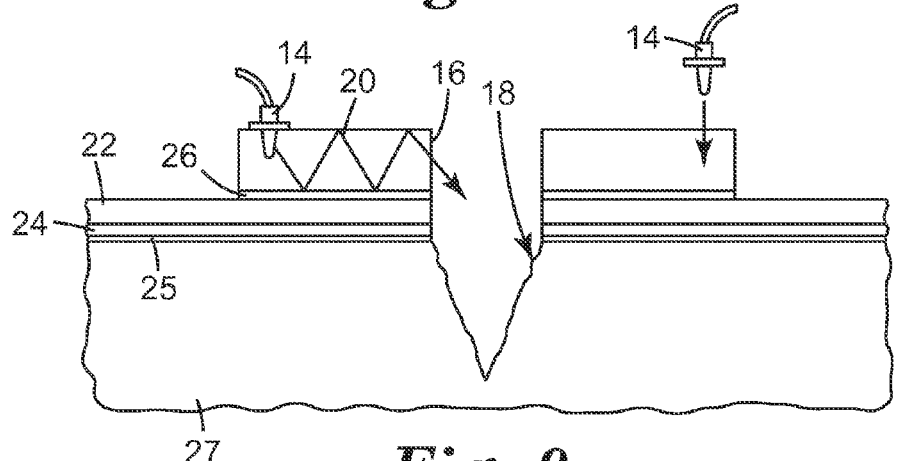
FIG. 9 shows a schematic cross-section of an exemplary medical article disposed on a patient showing illumination from an incised edge of the incise drape.

As exemplified by FIG. 9, in a typical surgical procedure the tissue of a patient 27 is coated with a presurgical skin preparation 25, an incise drape including a flexible polymeric film 22 and a pressure sensitive adhesive 24 is adhered to the presurgical skin preparation 25, a conformable polymeric (e.g., viscoelastic) lightguide layer 20 coated with a pressure sensitive adhesive 26 is adhered to the flexible polymeric film 22 of the incise drape, and LED push pins 14 are inserted into the conformable polymeric lightguide layer 20. An incision is made through all these skin coverings (presurgical skin preparation, incise drape, and conformable polymeric lightguide layer) into the tissue 27 thereby forming an incisional opening 18. Upon powering of the LED push pins 14 light travels through the conformable polymeric lightguide layer 20 along path indicated by the arrow and is emitted at the incisional edge 16 of the conformable polymeric lightguide layer 20. This light can be directed into the incisional opening by the practitioner through the process of retraction.

Flexible Polymeric Films

Useful flexible polymeric films are preferably transparent or translucent polymeric material. The material of the flexible films preferably allows for moisture evaporation through the film during prolonged surgeries. Flexible polymeric films of the present invention are typically provided in the form of conventional surgical incise drapes. Thus, herein, the term "incise drape" may refer to a conventional incise drape (e.g., a flexible polymeric film used in surgical procedures—one without a conformable polymeric lightguide layer as described herein) or it may refer to a medical article of the present invention (e.g., a conformable polymeric lightguide layer optionally disposed on a flexible polymeric film) used in surgical procedures.

Incise drapes are commonly used in surgical procedures to minimize exposure of the surgical wound to bacterial contamination from bacteria on the patient's skin. Draping of the surgical site provides a sterile work surface and helps minimize the transfer of microorganisms between non-sterile areas and the surgical wound. These measures also may help protect health care professionals from exposure to pathogens in the patient's blood and other body fluids. Importantly, incise drapes also may be employed to hold other articles such as fabric drapes securely to the operative site.

For proper functioning of a surgical incise drape, the incise drape is wrinkle-free after it is applied, especially directly at the incision point in order for the practitioner (e.g., surgeon) to be able to make a clean surgical incision. Wrinkles in the drape make it difficult for the practitioner to see through to the skin (transparency or translucency and visibility are important). Furthermore, if the incise drape includes wrinkles, the incise drape may not prevent bacteria on the skin from getting into the wound due to fluid channeling under the drape in these wrinkles. Maintaining a sterile surface at the point of incision helps prevent surgical wound infections.

The flexible polymeric film of a conventional incise material is usually a clear polymeric film with an adhesive on one side that is covered with a release liner. Examples of suitable incise drapes include those conventional incise drapes available under the tradenames STERI-DRAPE and IOBAN from 3M Company, St. Paul, Minn. Such drapes are substantially clear (transparent or translucent) and include a flexible film with one major surface coated with a pressure sensitive adhesive that adheres securely to wound edges, which assists in maintaining the barrier to skin flora. Such drapes conform to the body contours. Other conventional incise drapes are available from suppliers such as T.J. Smith and Nephew Ltd., Medline, and Cardinal, for example. Suitable incise drapes are described, for example, in U.S. Pat. Nos. 4,310,509; 4,323,557; 4,452,845; 4,584,192; 5,803,086; 5,979,450; 5,985,395; 6,939,936; Re. 31,886; and Re. 31,887.

Typically incise drapes are formed from a transparent or translucent flexible polymeric material. The material preferably allows for moisture evaporation through the film during prolonged surgeries. Particularly suitable materials for incise drapes include polyolefins, such as low density polyethylene and particularly metallocene polyethylenes (e.g., that available under the tradename ENGAGE polyethylenes from Dow Chemical Co.), polyurethanes such as polyester or polyether polyurethanes (e.g., that available under the tradename ESTANE thermoplastic polyurethane from B.F. Goodrich, Cleveland, Ohio), polyesters such as polyether polyester (e.g., that available under the tradename HYTREL polyester elastomer from Du Pont Co., Wilmington, Del.), and polyamides such as polyether polyamides (e.g., that available under the tradename PEBAX Resins from ELF Atochem, North America, Inc., Philadelphia, Pa.). Combinations of such materials can be used in the flexible polymeric films, including blends, copolymers, and laminates of such materials. Furthermore, the film is flexible, and preferably somewhat elastomeric, to improve conformability when applied to a patient. For these reasons, the preferred films are polyurethanes, polyether polyesters, polyether polyamides, or combinations thereof. The film will typically have a thickness of no greater than 200 microns, often no greater than 130 microns, and even more often no greater than 52 microns. The film will typically have a thickness (between first and second major surfaces) of at least 6 microns, and often at least 13 microns.

In certain embodiments, at least a major portion of at least one surface of the flexible film is coated with a pressure sensitive adhesive. Although the entire length of the flexible film is coated with the adhesive, any major portion may be coated that allows the surgical incise drape to serve its useful function, e.g., the adhesive need not coat the entire width or length of the drape. For example, non-coated portions may be included at any of the edges of the flexible film to assist in removal of the drape from the patient or to assist in attachment of a handle to the film. The adhesive coating the flexible film is preferably a tacky pressure sensitive adhesive at body temperature that will adhere aggressively to the skin. Uniform attachment to the skin surface helps maintain a sterile surgical field. Aggressive adhesives are preferred due to the stress the film is under during surgery as a result of the retraction of the wound, the warm moist environment, and the abrasion the film may encounter as the surgeon's hands and instruments move in and out of the wound.

Suitable pressure sensitive adhesives are skin compatible and include those described, for example, in U.S. Pat. Nos. 4,310,509, 4,323,557, 6,216,699, and 5,829,422, as well as PCT Publication Nos. WO 00/56828 and WO 00/78885. Wet-stick pressure sensitive adhesives can also be used, such as that described in U.S. Pat. No. 6,855,386. Suitable pressure sensitive adhesives include a polymeric resin composition that can be coatable, for example, by a hot melt process, the components of which are selected to provide the desired adhesive properties of the ultimate adhesive composition. Examples of pressure sensitive adhesive compositions useful in the present invention include, for example, those based on natural rubbers, synthetic rubbers, styrene block copolymers including but not limited to Styrene-Isoprene-Styrene (SIS), styrene-butadiene, styrene-isoprene and derivatives thereof such as those available from Kraton Polymers under the KRATON tradename, polyvinyl ethers, poly (meth)acrylates (including both acrylates and methacrylates), polyolefins such as polyalpha olefins, silicones, and blends or mixtures thereof. Particularly preferred adhesive compositions are based on poly(meth)acrylates (including both acrylates and methacrylates). The polyacrylates may also comprise other vinylic non-acrylate monomers such as but not limited to N-vinyl lactams, (meth)acrylamides, styrene, methylvinyl ether, polystyrene macromers, vinyl acetate, and the like. The pressure sensitive adhesive will typically have a thickness of no greater than 200 microns, often no greater than 150 microns, more often no greater than 100 microns, and even more often no greater than 50 microns. The pressure sensitive adhesive will typically have a thickness of at least 10 microns, often at least 20 microns, and even more often at least 30 microns.

The pressure sensitive adhesive may be made from a formulation of polymers that is inherently tacky. If desired, tackifiers may be added to a base polymeric formulation to form pressure sensitive adhesives. Useful tackifiers include, for example, rosin ester resins, aromatic hydrocarbon resins, aliphatic hydrocarbon resins, and terpene resins. Other materials can be added for special purposes, including, for example, oils, plasticizers, antioxidants, ultraviolet ("UV") stabilizers, hydrogenated butyl rubber, pigments, dyes, hydrocolloid particles such as those used in bioadhesive compositions and wound dressings disclosed in U.S. Pat. Nos. 5,750,134 and 5,633,010, additional antimicrobial agents, antioxidants, and curing agents.

Some incise drapes, such as that available under the tradename IOBAN, contain an antimicrobial agent, preferably iodophor, in the adhesive. The addition of antimicrobials to the drape adhesive provides the added benefit of helping to further minimize the potential of surgical infections by the maintenance of a bactericidal/bacteriostatic environment against the skin to greatly reduce the number of bacteria. Suitable optional antimicrobial agents are described, for example, in U.S. Pat. No. 5,369,155, at column 12, lines 32-39, which includes iodine and iodophors. For example, such antimicrobial agents that may optionally be incorporated in the pressure sensitive adhesive include alpha-hydroxyacids, such as but not limited to lactic acid, malic acid, citric acid, 2-hydroxybutanoic acid, 3-hydroxybutanoic acid, mandelic acid, gluconic acid, tartaric acid, as well as derivatives thereof (e.g., compounds substituted with hydroxyls, phenyl groups, hydroxyphenyl groups, alkyl groups, halogens, as well as combinations thereof); betahydroxyacids such as salicylic acid; C8-C18 fatty acids; C8-C18 sulfonic acids and there salts; quaternary ammonium surfactants having at least one alkyl chain of at least 8 carbon atoms and/or a benzyl group; parachlorometaxylenol (PCMX); triclosan; hexachlorophene; fatty acid monoesters of glycerin and propylene glycol, such as but not limited to glycerol monolaurate, glycerol monocaprylate, glycerol monocaprate, propylene glycol monolaurate, propylene glycol monocaprylate, propylene glycol monocaprate; phenols; polyquaternary amines, such as but not limited to polyhexamethylene biguanide; quaternary ammonium silanes having at least one alkyl chain of at least 8 carbon atoms; silver and silver salts, such as but not limited to silver chloride, silver oxide, and silver sulfadiazine; methyl, ethyl, propyl, and butyl parabens; octenidene; compounds that generate hydrogen peroxide such as perborates, complexes of hydrogen peroxide with polyvinylpyrrolidone (e.g., Peroxydone from ISP), natural oils such as tea tree oil, grape fruit seed extract, and the like, as well as combinations thereof.

Conventional surgical incise drapes typically have a release liner against the adhesive to protect the sterile adhesive surface prior to use. The release liner could be made of a variety of materials such as paper, plastic coated paper, plastic film, woven, non-woven, or knit textiles, as well as film textile laminates. Preferred release liner materials include clear polymeric liners that allow the clinician to see through to the patient and thus accurately place the film. Preferred clear polymeric liners include polyolefins such as polyethylene and polypropylene, or polyester liners, as well as laminates such as polyolefin coated polyester. For products intended for gamma sterilization, use of a paper, polyethylene, polyester, or polyethylene coated polyester liner is preferred.

For those drapes wound onto themselves without release liners, the flexible films are usually treated on the back side with a release coating such as silicone. If used such that the viscoelastic layer is disposed on the back side of the flexible film, no release coating would typically be used, thereby ensuring good adhesion between the film and the viscoelastic layer. Alternatively, a viscoelastic layer could be designed to stick to such a release coating. For instance, if it is a silicone release coating, a silicone PSA lightguide could be used.

The flexible film may also be treated prior to coating of the pressure sensitive adhesive thereon to enhance the adhesion of the adhesive to the flexible film substrate. Treatments useful for enhancing the adhesion of a pressure sensitive adhesive and/or the viscoelastic layer to the flexible film include chemical priming and corona treatment.

Presurgical Skin Preparations and Barrier Films

Presurgical skin preparations can be of a variety of well-known types. As used herein, a presurgical skin preparation includes antiseptic skin preparations, antiseptic skin preparations having polymeric film formers, and film forming preparations useful as microbial sealants or barriers. A presurgical polymeric barrier film can also be used, such as that available under the trade designation INTEGUSEAL (a cyanoacrylate applied directly to skin in place of an incise drape) from Kimberly Clark. Other presurgical skin preparations and barrier films are described in a number of patents including, U.S. Pat. Nos. 4,584,192; 4,542,012; 7,459,167; and 7,030,203, as well as U.S. Patent Application Publication Nos. 2008/0046004 and 2007/0147947. Such presurgical skin preparation and/or polymeric barrier film could be used directly on the skin in which case the medical article is adhered to the surgical skin preparation and/or barrier film.

Such presurgical skin preparations and/or polymeric barrier films could be formulated to facilitate extraction of light (or retard it) by adjusting the refractive index of the film formed upon application and drying. For example, if the skin preparation is a liquid that is applied and then dried, if the refractive index of the resulting film is lower than the lightguide, it will promote TIR within the guide. If the preparation is of an index higher than the lightguide, it will couple light out of the lightguide and onto the surface of the skin. If the preparation contains some extracting mechanism, it could cause light to be extracted and re-directed. If the preparation contains some fluorescent material, it could stimulate colored light emission in response to illumination from the light emitted by the lightguide.

Methods of Use

Methods of the present invention involve illuminating tissue during a surgical procedure or other medical applications.

In certain embodiments, the methods include: applying a conventional surgical incise drape to a patient over a presurgical skin preparation followed by applying a conformable polymeric lightguide layer over the conventional surgical incise drape; or applying the conformable polymeric lightguide layer to a conventional surgical incise drape and then applying the composite incise drape to the patient; or applying a conformable polymeric lightguide layer to the tissue (e.g., skin) over a presurgical skin preparation followed by applying a conventional surgical incise drape over the conformable polymeric lightguide layer; or applying a conformable polymeric lightguide layer over a presurgical skin preparation such as DuraPrep (without the use of a conventional surgical incise drape); or applying a conformable polymeric lightguide layer over a presurgical polymeric barrier film such as that available under the trade designation INTEGUSEAL (a cyanoacrylate applied directly to skin in place of an incise drape) from Kimberly Clark. Thus, "adhering" a medical article (e.g., incise drape) of the present invention "to a patient" may involve any of these alternative methods.

In one embodiment, the present invention provides a method of illuminating tissue of a patient during a surgical procedure, the method including: providing an incise drape comprising: a conformable polymeric lightguide layer having opposite first and second major surfaces; and a light source optically coupled to the conformable polymeric lightguide layer; wherein light emitted by the light source enters the conformable polymeric lightguide layer and is transported within the conformable polymeric lightguide layer by total internal reflection; adhering the incise drape to the patient such that it conforms to the shape of the tissue of the patient; making an incision through the incise drape into the tissue to form a cut edge of the incise drape from which light is emitted at the cut edge; and retracting the tissue and incise drape along the incision in a manner such that the light emitted from the cut edge of the incise drape illuminates the tissue in and around the incision.

In another embodiment, the present invention provides a method of illuminating tissue of a patient, the method including: providing a medical article comprising: a conformable polymeric lightguide layer having opposite first and second major surfaces; and a light source optically coupled to the conformable polymeric lightguide layer; wherein light emitted by the light source enters the conformable polymeric lightguide layer and is transported within the conformable polymeric lightguide layer by total internal reflection; adhering the medical article to the patient such that it conforms to the shape of the tissue of the patient and illuminates the tissue of the patient using light emitted from a major surface and/or an edge of the medical article.

In certain methods, the light comprises UV light. In certain methods, the light comprises single wavelength light. In certain methods, the light is emitted from an edge of the medical article.

In certain methods, the medical article used includes a flexible polymeric film having opposite first and second major surfaces, wherein the conformable polymeric lightguide layer is disposed on the first major surface of the film.

In another method, the present invention provides a method of indicating excessive tissue bending or folding during a surgical procedure, the method comprising: providing an incise drape comprising: a conformable polymeric lightguide layer having opposite first and second major surfaces, a light source, and wherein light emitted by the light source enters the conformable polymeric lightguide layer and is transported within the conformable polymeric lightguide layer by total internal reflection; adhering the incise drape to the patient such that it conforms to the shape of the tissue of the patient; making an incision through the incise drape into the tissue to form a cut edge of the incise drape from which light is emitted at the cut edge; and retracting the tissue and incise drape along the incision causing the tissue (e.g., skin) adjacent to the incision to wrinkle; wherein the tissue wrinkling causes the total internal reflection angle of the lightguide to be exceeded, causing light emitted from the cut edge to be reduced and light emitted from a major surface of the incise drape along the wrinkled area to be increased, thereby indicating that excessive tissue bending may be occurring in the tissue in and around the incision. In this way, a medical article of the present invention can act as a sensor to indicate that a skin surface is too wrinkled by illuminating the sinusoidal wrinkles with more light, and with less light at the cut edge. This would provide an indication that the skin is being damaging by excessive retraction.

Other uses of the medical articles of the present invention include the treatment of topical conditions using light and/or heat such as wounds, acne, rosacea, topical infections, age spots, varicose veins, etc. Also, the medical article could be a patch for distributing desired wavelength of light to treat jaundice in infants, for example.

Medical articles of the present invention could be used to deliver IR light for heating tissue. For example, the medical articles could be thermal patches that use IR light, which would be significantly more desirable than menthol-type patches.

Medical articles of the present invention could be used to enhance transdermal drug penetration, for example, if IR were used to warm the skin. Warming the area may be used to enhance transdermal drug penetration. The drug can be pre-applied to skin or incorporated into or onto the medical article.

The production of heat could also occur using medical articles of the present invention in which shorter wavelength light is transmitted into a down converting material that absorbs light energy and creates heat.

Medical articles of the present invention could be used for illumination to evaluate for skin cancer or, to find other sub-dermal structures such as veins and arteries.

Medical articles of the present invention could incorporate an antimicrobial and a needle or catheter inserted through it into a patient. Alternatively, the articles could have an array of holes through which a needle or catheter can pass, or the articles can be shaped to have a slot much like a key hole through which a needle or catheter can be inserted.

In certain embodiments, medical articles of the present invention can be provided as multiple pieces. For example, in one embodiment, two or more medical articles including a viscoelastic lightguide layer can be applied to the skin of a patient, one or more on either side of an incision site, thereby avoiding cutting through the viscoelastic lightguide layers.

ILLUSTRATIVE EMBODIMENTS OF THE INVENTION

1. A medical article comprising:
a flexible polymeric film having opposite first and second major surfaces;
a viscoelastic lightguide layer disposed on a major surface of the film; and
a light source optically coupled to the viscoelastic lightguide layer,
wherein light emitted by the light source enters the viscoelastic lightguide layer and is transported within the viscoelastic lightguide layer by total internal reflection; and
wherein the medical article is sterilized or sterilizable and conformable to a body part of a patient.
2. The medical article of embodiment 1 wherein the light source comprises light emitting diodes.
3. The medical article of embodiment 2 wherein the light emitting diodes are provided as push pins or in a strip.
4. The medical article of any one of the preceding embodiments wherein the light source is directly coupled to the viscoelastic lightguide layer.
5. The medical article of any one of the preceding embodiments wherein the flexible polymeric film comprises a polyolefin, a polyurethane, a polyester, a polyamide, or combinations thereof.
6. The medical article of any one of the preceding embodiments wherein the flexible polymeric film is elastomeric.
7. The medical article of embodiment 6 wherein the flexible polymeric film comprises a polyurethane, a polyether polyester, a polyether polyamide, or combinations thereof.
8. The medical article of any one of the preceding embodiments wherein the flexible polymeric film had a thickness of no greater than 200 microns between the first and second major surfaces.
9. The medical article of any one of the preceding embodiments wherein the flexible polymeric film is provided as a conventional surgical incise drape.
10. The medical article of any one of the preceding embodiments wherein the flexible polymeric film, the viscoelastic lightguide layer, or both comprises a pressure sensitive adhesive disposed on at least a portion of at least one major surface thereof.
11. The medical article of any one of the preceding embodiments wherein the viscoelastic lightguide layer comprises at least one active agent.
12. The medical article of embodiment 11 wherein the active agent comprises an antimicrobial, an anti-irritant, an active to promote wound healing, an analgesic, a skin lighting agent, or combinations thereof.
13. The medical article of embodiment 12 wherein the active agent comprises iodine or an iodophor.

14. The medical article of any one of the preceding embodiments wherein at least one surface of the medical article has an active agent disposed thereon.

15. The medical article of any one of the preceding embodiments wherein at least one surface of the viscoelastic lightguide layer comprises a plurality of features oriented to extract light being transported within the lightguide layer.

16. The medical article of embodiment 15 wherein the viscoelastic lightguide layer comprises a (meth)acrylate, a rubber, a silicone, a polyurethane, a polyester, a polyurea, a polyamide, a polyolefin, or combinations thereof.

17. The medical article of any one of the preceding embodiments wherein the viscoelastic lightguide layer comprises a pressure sensitive adhesive.

18. The medical article of embodiment 17 wherein the pressure sensitive adhesive comprises a natural rubber, a synthetic rubber, a styrene block copolymer, a (meth)acrylic block copolymer, a polyvinyl ether, a polyolefin, a poly(meth)acrylate, or combinations thereof.

19. The medical article of any one of the preceding embodiments further comprising a release liner disposed on the viscoelastic lightguide layer.

20. The medical article of any one of the preceding embodiments wherein the light source emits UV light.

21. The medical article of any one of the preceding embodiments wherein the light source emits IR light.

22. The medical article of any one of the preceding embodiments adhered to the skin of a patient.

23. A medical article adhered to the skin of a patient, the medical article comprising:
 a flexible polymeric film having opposite first and second major surfaces;
 a viscoelastic layer disposed on a major surface of the film;
 a light source, and
 a lightguide, wherein light emitted by the light source enters the lightguide and is transported within the lightguide by total internal reflection;
 wherein the medical article is adhered to skin of the patient sufficiently for the skin to function as an extractor of the light.

24. The medical article of embodiment 23 wherein the viscoelastic layer is the lightguide, and wherein light emitted by the light source enters the viscoelastic lightguide and is transported within the viscoelastic lightguide by total internal reflection.

25. The medical article of embodiment 24 wherein at least one surface of the viscoelastic lightguide comprises a plurality of features oriented to extract light being transported within the viscoelastic lightguide.

26. The medical article of embodiment 23 wherein the viscoelastic layer is disposed on the lightguide, and wherein light emitted by the light source enters the lightguide and is transported within the lightguide by total internal reflection.

27. The medical article of embodiment 26 wherein an interface formed between the lightguide and the viscoelastic layer comprises a plurality of features oriented to extract light being transported within the lightguide.

28. The medical article of any one of embodiments 23 through 27 wherein the thickness of the viscoelastic layer is non-uniform.

29. The medical article of any one of embodiments 23 through 28 wherein the flexible polymeric film is elastomeric.

30. A medical article adhered to a patient, the medical article comprising:
 a flexible polymeric film having opposite first and second major surfaces;
 a conformable polymeric layer disposed on a major surface of the film;
 a light source; and
 a lightguide, wherein light emitted by the light source enters the lightguide and is transported within the lightguide by total internal reflection;
 wherein the medical article is adhered to the patient.

31. The medical article of embodiment 30 wherein the medical article is adhered to a presurgical skin preparation or barrier film on the skin of the patient.

32. The medical article of embodiment 30 wherein the conformable polymeric layer is the lightguide, and wherein light emitted by the light source enters the conformable polymeric lightguide and is transported within the conformable polymeric lightguide by total internal reflection.

33. The medical article of embodiment 32 wherein at least one surface of the conformable polymeric lightguide comprises a plurality of features oriented to extract light being transported within the conformable polymeric lightguide.

34. The medical article of embodiment 30 wherein the conformable polymeric layer is disposed on the lightguide, and wherein light emitted by the light source enters the lightguide and is transported within the lightguide by total internal reflection.

35. The medical article of embodiment 34 wherein an interface formed between the lightguide and the conformable polymeric layer comprises a plurality of features oriented to extract light being transported within the lightguide.

36. A method of illuminating tissue of a patient during a surgical procedure, the method comprising:
 providing an incise drape comprising:
  a conformable polymeric lightguide layer having opposite first and second major surfaces; and
  a light source optically coupled to the conformable polymeric lightguide layer;
  wherein light emitted by the light source enters the conformable polymeric lightguide layer and is transported within the conformable polymeric lightguide layer by total internal reflection;
 adhering the incise drape to the patient such that it conforms to the shape of the tissue of the patient;
 making an incision through the incise drape into the tissue to form a cut edge of the incise drape from which light is emitted at the cut edge; and
 retracting the tissue and incise drape along the incision in a manner such that the light emitted from the cut edge of the incise drape illuminates the tissue in and around the incision.

37. The method of embodiment 36 wherein the light comprises UV light.

38. The method of embodiment 36 or embodiment 37 wherein the light comprises a narrow spectrum of wavelengths.

39. The method of any one of embodiments 36 through 38 wherein the incise drape further comprises a flexible polymeric film having opposite first and second major surfaces, wherein the conformable polymeric lightguide layer is disposed on a major surface of the film.

40. The method of any one of embodiments 36 through 40 wherein the thickness of the conformable polymeric lightguide layer is non-uniform.

41. The method of any one of embodiments 36 through 40 wherein at least one surface of the conformable polymeric lightguide comprises a plurality of features oriented to extract light being transported within the conformable polymeric lightguide.

42. The method of any one of embodiments 36 through 41 wherein the conformable polymeric lightguide layer comprises a viscoelastic material.

43. The method of any one of embodiments 36 through 42 wherein the conformable polymeric lightguide layer comprises an elastic material.
44. A method of illuminating tissue of a patient, the method comprising:
  providing a medical article comprising:
    a conformable polymeric lightguide layer having opposite first and second major surfaces; and
    a light source optically coupled to the conformable polymeric lightguide layer;
    wherein light emitted by the light source enters the conformable polymeric lightguide layer and is transported within the conformable polymeric lightguide layer by total internal reflection;
  adhering the medical article to the patient such that it conforms to the shape of the tissue of the patient and illuminates the tissue of the patient using light emitted from a major surface and/or an edge of the medical article.
45. The method of embodiment 44 wherein the light is emitted from an edge of the medical article.
46. The method of embodiment 44 or embodiment 45 wherein the conformable polymeric lightguide layer comprises a viscoelastic material.
47. The method of embodiment 44 or embodiment 45 wherein the conformable polymeric lightguide layer comprises an elastic material.
48. A method of indicating excessive tissue bending during a surgical procedure, the method comprising:
  providing an incise drape comprising:
    a conformable polymeric lightguide layer having opposite first and second major surfaces; and
    a light source;
    wherein light emitted by the light source enters the conformable polymeric lightguide layer and is transported within the conformable polymeric lightguide layer by total internal reflection;
  adhering the incise drape to the patient such that it conforms to the shape of the tissue of the patient;
  making an incision through the incise drape into the tissue to form a cut edge of the incise drape from which light is emitted at the cut edge; and
  retracting the tissue and incise drape along the incision causing the tissue adjacent to the incision to wrinkle;
  wherein the tissue wrinkling causes the total internal reflection angle of the lightguide to be exceeded, causing light emitted from the cut edge to be reduced and light emitted from a major surface of the incise drape along the wrinkled area to be increased, thereby indicating that excessive tissue bending may be occurring in the tissue in and around the incision.
49. The method of embodiment 48 wherein the conformable polymeric lightguide layer comprises a viscoelastic material.
50. The method of embodiment 48 wherein the conformable polymeric lightguide layer comprises an elastic material.

EXAMPLES

Objects and advantages of this invention are further illustrated by the following examples, but the particular materials and amounts thereof recited in these examples, as well as other conditions and details, should not be construed to unduly limit this invention.

Example 1

3M IOBAN 2 Antimicrobial Incise Drape (3M Company, St. Paul, Minn.) was laminated on the backside with 3M VHB tape 4918 clear acrylic bonding adhesive, 2 mm (80 mils) thick. To the edges of this 2 mm thick PSA was attached a wedge of 3M VIKUITI Enhanced Specular Reflector (ESR) film, that contained a string of side-emitting LED lights, wired to a 12 volt DC power supply. The top surface of the thick PSA lightguide was covered by a 50 micron thick (1.95 mil) layer of transparent bi-axially oriented polypropylene (BOPP) film, prepared as described in PCT Publication No. WO 2010/021796. When the power was turned on, the light entered the 2 mm (80 mil) thick PSA and could be seen to exit the open end of the lightguide (LED's injected into one edge only). When this BOPP/PSA/Ioban sandwich laminate was cut with a razor, light was visibly seen exiting the new cut surface.

Example 2

3M IOBAN 2 Antimicrobial Incise Drape was laminated on the backside with a 1 mm (40 mils) 3M VHB tape 4910 clear acrylic bonding adhesive. To the edges of this 1 mm thick PSA was attached a wedge of 3M ESR film that contained a string of side-emitting LED lights wired to a 12 volt DC power supply. The top surface of the thick PSA lightguide was covered by a layer of transparent BOPP. When the power was turned on, the light entered the 1 mm thick PSA and could be seen to exit the open end of the lightguide (LED's injected into one edge only). When the BOPP/PSA/Ioban sandwich laminate was cut with a razor, light was visibly seen exiting the new cut surface.

Example 3

An LED could be encapsulated into a transparent/translucent rigid, solid shape of polycarbonate or poly(methyl methacrylate) (PMMA) with a molded pointed "needle tip." The encapsulated LED, utilizing industry standard clip on electrical connectors such as those used in 3M RED DOT electrode products, could simply be "pushed" into the thick lightguide PSA layer at any desired point to give custom illumination to the drape site through the PSA lightguide. This is shown in FIG. 9.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A medical article comprising:
  a flexible polymeric film having opposite first and second major surfaces;
  a viscoelastic lightguide layer disposed on a major surface of the film; and
  a light source optically coupled to the viscoelastic lightguide layer,
    wherein light emitted by the light source enters the viscoelastic lightguide layer and is transported within the viscoelastic lightguide layer by total internal reflection; and
    wherein the medical article is sterilized or sterilizable and conformable to a body part of a patient.

2. The medical article of claim 1 wherein the flexible polymeric film, the viscoelastic lightguide layer, or both comprises a pressure sensitive adhesive disposed on at least a portion of at least one major surface thereof.

3. The medical article of claim 1 wherein the viscoelastic lightguide layer comprises at least one active agent.

4. The medical article of claim 1 wherein at least one surface of the medical article has an active agent disposed thereon.

5. The medical article of claim 1 wherein at least one surface of the viscoelastic lightguide layer comprises a plurality of features oriented to extract light being transported within the lightguide layer.

6. The medical article of claim 1 wherein the viscoelastic lightguide layer comprises a pressure sensitive adhesive.

7. The medical article of claim 1 further comprising a release liner disposed on the viscoelastic lightguide layer.

8. The medical article of claim 1 adhered to the skin of a patient.

9. A method of illuminating tissue of a patient, the method comprising:
   providing the medical article of claim 1;
   adhering the medical article to the patient such that it conforms to the shape of the tissue of the patient and illuminates the tissue of the patient using light emitted from a major surface and/or an edge of the medical article.

10. The method of claim 9 wherein the medical article is an incise drape, the method further comprising:
    making an incision through the incise drape into the tissue to form a cut edge of the incise drape from which light is emitted at the cut edge; and
    retracting the tissue and incise drape along the incision in a manner such that the light emitted from the cut edge of the incise drape illuminates the tissue in and around the incision.

11. The method of claim 10 wherein retracting the tissue and incise drape along the incision causes the tissue adjacent to the incision to wrinkle;
    wherein the tissue wrinkling causes the total internal reflection angle of the lightguide to be exceeded, causing light emitted from the cut edge to be reduced and light emitted from a major surface of the incise drape along the wrinkled area to be increased, thereby indicating that excessive tissue bending may be occurring in the tissue in and around the incision.

12. A medical article adhered to a patient, the medical article comprising:
    a flexible polymeric film having opposite first and second major surfaces;
    a conformable polymeric layer disposed on a major surface of the film, wherein the conformable polymeric layer is a viscoelastic layer;
    a light source; and
    a lightguide, wherein light emitted by the light source enters the lightguide and is transported within the lightguide by total internal reflection;
    wherein the viscoelastic layer is disposed on the lightguide; and
    wherein the medical article is adhered to the patient sufficiently for the skin to function as an extractor of the light.

13. The medical article of claim 12 wherein an interface formed between the lightguide and the viscoelastic layer comprises a plurality of features oriented to extract light being transported within the lightguide.

* * * * *

UNITED STATES PATENT AND TRADEMARK OFFICE
CERTIFICATE OF CORRECTION

PATENT NO. : 8,758,237 B2  
APPLICATION NO. : 13/391221  
DATED : June 24, 2014  
INVENTOR(S) : Audrey A. Sherman et al.

Page 1 of 1

It is certified that error appears in the above-identified patent and that said Letters Patent is hereby corrected as shown below:

Title page 2  
Item (56) References Cited under OTHER PUBLICATIONS  
Line 8, "Meachanical" should read --Mechanical--.  
Line 18, "Antimicobial" should read --Antimicrobial--.  
Line 21, "Hydrolloid" should read --Hydrocolloid--.

In the Specification  
Column 1  
Line 26, "refraction" should read --retraction--.

Column 16  
Line 7, "vinylaceate," should read --vinylacetate--.

Column 17  
Line 67, "propianate]" should read --propionate]--.

Column 18  
Line 66, "terpentine" should read --turpentine--.

Column 19  
Lines 16-17, "hyrosilylation" should read --hydrosilylation--.

Column 21  
Line 46, "bephenyl" should read --biphenyl--.

Column 22  
Line 37, "include include" should read --include--.  
Line 63, "octenidene;" should read --octenidine--.

Column 29  
Line 27, "octenidene;" should read --octenidine--.

Signed and Sealed this  
Twenty-second Day of September, 2015

Michelle K. Lee  
*Director of the United States Patent and Trademark Office*